US012758330B2

(12) United States Patent
Schuh et al.

(10) Patent No.: US 12,758,330 B2
(45) **Date of Patent: *Oct. 13, 2026**

(54) LENGTH CONSERVATIVE SURGICAL INSTRUMENT

(71) Applicant: Auris Health, Inc., Redwood City, CA (US)

(72) Inventors: Travis Schuh, Los Altos, CA (US); Edward J. Menard, San Carlos, CA (US); Bruce R. Woodley, Palo Alto, CA (US); Matthew Reagan Williams, Walnut Creek, CA (US); Spencer James Witte, Los Altos, CA (US)

(73) Assignee: Auris Health, Inc., Santa Clara, CA (US)

( * ) Notice: Subject to any disclaimer, the term of this patent is extended or adjusted under 35 U.S.C. 154(b) by 844 days.

This patent is subject to a terminal disclaimer.

(21) Appl. No.: 18/098,657

(22) Filed: Jan. 18, 2023

(65) Prior Publication Data

US 2023/0210616 A1 Jul. 6, 2023

Related U.S. Application Data

(63) Continuation of application No. 16/900,009, filed on Jun. 12, 2020, now Pat. No. 11,564,759, which is a
(Continued)

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/37* (2016.02); *A61B 34/71* (2016.02); *A61B 34/74* (2016.02);
(Continued)

(58) Field of Classification Search
CPC ......... A61B 34/30; A61B 34/70; A61B 34/71; A61B 2034/305; A61B 2034/306;
(Continued)

(56) References Cited

U.S. PATENT DOCUMENTS 2,556,601 A 6/1951 Schofield
2,566,183 A 8/1951 Forss
(Continued)

FOREIGN PATENT DOCUMENTS

CN 101161426 4/2008
CN 103037799 4/2011
(Continued)

OTHER PUBLICATIONS

Korean Decision of Patent Grant; Application No. 10-2018-7028118; May 16, 2023; 3 pages.
(Continued)

*Primary Examiner* — Diane D Yabut
(74) *Attorney, Agent, or Firm* — FBT Gibbons LLP

(57) ABSTRACT

A surgical instrument is described that includes a surgical effector moving with N degrees of freedom for manipulation of objects at a surgical site during surgical procedures. The surgical effector can be manipulated by actuating a first input controller to control a length of a first cable segment to move the surgical effector in at least one degree of freedom of movement and actuating a second input controller to control a length of a second cable segment to move the surgical effector in the at least one degree of freedom of movement. The surgical effector can be manipulated by moving a differential that couples the first and second input controllers together to conserve a length of cable between the first input controller and the second input controller.

20 Claims, 14 Drawing Sheets

Related U.S. Application Data continuation of application No. 15/970,750, filed on May 3, 2018, now Pat. No. 10,682,189, which is a continuation of application No. 15/353,576, filed on Nov. 16, 2016, now Pat. No. 9,962,228, which is a continuation of application No. PCT/US2016/049775, filed on Aug. 31, 2016.

(51) Int. Cl.
*A61B 34/37* (2016.01)
*A61B 17/00* (2006.01)
*B25J 9/16* (2006.01)

(52) U.S. Cl.
CPC ............... *A61B 2017/00477* (2013.01); *A61B 2034/305* (2016.02); *A61B 2034/715* (2016.02); *A61B 2034/742* (2016.02); *A61B 2034/743* (2016.02); *B25J 9/1641* (2013.01)

(58) Field of Classification Search
CPC ...... A61B 2034/715; A61B 2017/2902; A61B 2017/2927; F16H 19/06; F16H 2019/0609; B25J 9/1641
See application file for complete search history.

(56) References Cited

U.S. PATENT DOCUMENTS 2,623,175 A 12/1952 Finke
2,730,699 A 1/1956 Gratian
2,884,808 A 5/1959 Mueller
3,294,183 A 12/1966 Riley et al.
3,472,083 A 10/1969 Schnepel
3,513,724 A 5/1970 Box
3,595,074 A 7/1971 Johnson
3,734,207 A 5/1973 Fishbein
3,739,923 A 6/1973 Totsuka
3,784,031 A 1/1974 Nitu
3,790,002 A 2/1974 Guilbaud et al.
3,921,536 A 11/1975 Savage
3,926,386 A 12/1975 Stahmann
4,141,245 A 2/1979 Brandstetter
4,241,884 A 12/1980 Lynch
4,243,034 A 1/1981 Brandt
4,351,493 A 9/1982 Sonnek
4,357,843 A 11/1982 Peck et al.
4,384,493 A 5/1983 Grunbaum
4,507,026 A 3/1985 Lund
4,530,471 A 7/1985 Inoue
4,555,960 A 12/1985 King
4,688,555 A 8/1987 Wardle
4,745,908 A 5/1988 Wardle
4,784,150 A 11/1988 Voorhies et al.
4,857,058 A 8/1989 Pavton
4,907,168 A 3/1990 Boggs
4,945,790 A 8/1990 Golden
5,207,128 A 5/1993 Albright
5,234,428 A 8/1993 Kaufman
5,256,150 A 10/1993 Quiachon et al.
5,277,085 A 1/1994 Tanimura et al.
5,350,101 A 9/1994 Godlewski
5,426,687 A 6/1995 Goodall et al.
5,507,725 A 4/1996 Savage et al.
5,524,180 A 6/1996 Wang et al.
5,559,294 A 9/1996 Hoium et al.
5,709,661 A 1/1998 Van Egmond
5,767,840 A 6/1998 Selker
5,779,623 A 7/1998 Bonnell
5,792,135 A 8/1998 Madhani et al.
5,797,900 A 8/1998 Madhani
5,842,390 A 12/1998 Bouligny
5,855,583 A 1/1999 Wang et al.
5,921,968 A 7/1999 Lampropoulos et al.
5,967,934 A 10/1999 Ishida et al.
6,077,219 A 6/2000 Viebach
6,084,371 A 7/2000 Kress et al.
6,154,000 A 11/2000 Rastegar et al.
6,171,234 B1 1/2001 White et al.
6,185,478 B1 2/2001 Koakutsu et al.
6,272,371 B1 8/2001 Shlomo
6,289,579 B1 9/2001 Viza et al.
6,394,998 B1 5/2002 Wallace et al.
6,401,572 B1 6/2002 Provost
6,436,107 B1 8/2002 Wang et al.
6,487,940 B2 12/2002 Hart et al.
6,491,701 B2 12/2002 Tierney et al.
6,695,818 B2 2/2004 Wollschlager
6,726,675 B1 4/2004 Bevar
6,786,896 B1 9/2004 Madhani et al.
6,827,712 B2 12/2004 Tovey et al.
7,044,936 B2 5/2006 Harding
7,172,580 B2 2/2007 Hruska et al.
7,276,044 B2 10/2007 Ferry et al.
7,615,042 B2 11/2009 Beyar et al.
7,635,342 B2 12/2009 Ferry et al.
7,766,856 B2 8/2010 Ferry et al.
7,938,809 B2 5/2011 Lampropoulos et al.
7,972,298 B2 7/2011 Wallace et al.
7,974,674 B2 7/2011 Hauck et al.
7,998,020 B2 8/2011 Kidd et al.
8,052,636 B2 11/2011 Moll et al.
8,157,308 B2 4/2012 Pedersen
8,182,415 B2 5/2012 Larkin et al.
8,277,417 B2 10/2012 Fedinec et al.
8,291,791 B2 10/2012 Light et al.
8,414,505 B1 4/2013 Weitzner
8,425,465 B2 4/2013 Nagano
8,671,817 B1 3/2014 Bogusky
8,720,448 B2 5/2014 Reis et al.
8,746,252 B2 6/2014 McGrogan et al.
8,870,815 B2 10/2014 Bhat et al.
8,961,533 B2 2/2015 Stahler et al.
8,968,333 B2 3/2015 Yu et al.
8,992,542 B2 3/2015 Hagag et al.
9,173,713 B2 11/2015 Hart et al.
9,204,933 B2 12/2015 Reis et al.
9,259,281 B2 2/2016 Griffiths et al.
9,326,822 B2 5/2016 Lewis et al.
9,408,669 B2 8/2016 Kokish et al.
9,446,177 B2 9/2016 Millman et al.
9,452,018 B2 9/2016 Yu
9,457,168 B2 10/2016 Moll et al.
9,498,601 B2 11/2016 Tanner et al.
9,504,604 B2 11/2016 Alvarez
9,561,083 B2 2/2017 Yu et al.
9,622,827 B2 4/2017 Yu et al.
9,636,184 B2 5/2017 Lee et al.
9,636,483 B2 5/2017 Hart et al.
9,668,814 B2 6/2017 Kokish
9,713,509 B2 7/2017 Schuh et al.
9,727,963 B2 8/2017 Mintz et al.
9,737,371 B2 8/2017 Romo et al.
9,737,373 B2 8/2017 Schuh
9,744,335 B2 8/2017 Jiang
9,763,741 B2 9/2017 Alvarez et al.
9,788,910 B2 10/2017 Schuh
9,844,412 B2 12/2017 Bogusky et al.
9,867,635 B2 1/2018 Alvarez et al.
9,918,659 B2 3/2018 Chopra
9,918,681 B2 3/2018 Wallace et al.
9,931,025 B1 4/2018 Graetzel et al.
9,949,749 B2 4/2018 Noonan et al.
9,955,986 B2 5/2018 Shah
9,962,228 B2 5/2018 Schuh et al.
9,980,785 B2 5/2018 Schuh
9,993,313 B2 6/2018 Schuh et al.
9,993,614 B2 6/2018 Pacheco
10,016,900 B1 7/2018 Meyer et al.
10,022,192 B1 7/2018 Ummalaneni
10,046,140 B2 8/2018 Kokish et al.
10,080,576 B2 9/2018 Romo et al.
10,136,959 B2 11/2018 Mintz et al.
10,143,360 B2 12/2018 Roelle et al.

(56) References Cited

U.S. PATENT DOCUMENTS

| | | | |
|---|---|---|---|
| 10,145,747 | B1 | 12/2018 | Lin et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,213,264 | B2 | 2/2019 | Tanner et al. |
| 10,219,874 | B2 | 3/2019 | Yu et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,258,285 | B2 | 4/2019 | Hauck |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,383,765 | B2 | 8/2019 | Alvarez et al. |
| 10,398,518 | B2 | 9/2019 | Yu et al. |
| 10,405,939 | B2 | 9/2019 | Romo et al. |
| 10,405,940 | B2 | 9/2019 | Romo |
| 10,426,559 | B2 | 10/2019 | Graetzel et al. |
| 10,426,661 | B2 | 10/2019 | Kintz |
| 10,434,660 | B2 | 10/2019 | Meyer |
| 10,454,347 | B2 | 10/2019 | Covington et al. |
| 10,464,209 | B2 | 11/2019 | Ho et al. |
| 10,470,830 | B2 | 11/2019 | Hill |
| 10,478,595 | B2 | 11/2019 | Kokish |
| 10,482,599 | B2 | 11/2019 | Mintz et al. |
| 10,493,239 | B2 | 12/2019 | Hart et al. |
| 10,493,241 | B2 | 12/2019 | Jiang |
| 10,500,001 | B2 | 12/2019 | Yu et al. |
| 10,517,692 | B2 | 12/2019 | Eyre et al. |
| 10,524,866 | B2 | 1/2020 | Srinivasan |
| 10,524,867 | B2 | 1/2020 | Kokish et al. |
| 10,539,478 | B2 | 1/2020 | Lin |
| 10,543,047 | B2 | 1/2020 | Yu |
| 10,543,048 | B2 | 1/2020 | Noonan et al. |
| 10,555,778 | B2 | 2/2020 | Ummalaneni et al. |
| 10,556,092 | B2 | 2/2020 | Yu et al. |
| 10,569,052 | B2 | 2/2020 | Kokish et al. |
| 10,631,949 | B2 | 4/2020 | Schuh et al. |
| 10,639,108 | B2 | 5/2020 | Romo et al. |
| 10,639,109 | B2 | 5/2020 | Bovay et al. |
| 10,639,114 | B2 | 5/2020 | Schuh |
| 10,667,871 | B2 | 6/2020 | Romo et al. |
| 10,667,875 | B2 | 6/2020 | DeFonzo |
| 10,682,189 | B2 | 6/2020 | Schuh et al. |
| 10,687,903 | B2 | 6/2020 | Lewis et al. |
| 10,695,536 | B2 | 6/2020 | Weitzner et al. |
| 10,702,348 | B2 | 7/2020 | Moll et al. |
| 10,716,461 | B2 | 7/2020 | Jenkins |
| 10,743,751 | B2 | 8/2020 | Landey et al. |
| 10,744,035 | B2 | 8/2020 | Alvarez et al. |
| 10,751,140 | B2 | 8/2020 | Wallace et al. |
| 2001/0042643 | A1 | 11/2001 | Krueger et al. |
| 2002/0045905 | A1 | 4/2002 | Gerbi et al. |
| 2002/0098938 | A1 | 7/2002 | Milbourne et al. |
| 2002/0100254 | A1 | 8/2002 | Dharssi |
| 2002/0107573 | A1 | 8/2002 | Steinberg |
| 2002/0117017 | A1 | 8/2002 | Bernhardt et al. |
| 2002/0161355 | A1 | 10/2002 | Wollschlager |
| 2002/0161426 | A1 | 10/2002 | Lancea |
| 2002/0177789 | A1 | 11/2002 | Ferry et al. |
| 2003/0056561 | A1 | 3/2003 | Butscher et al. |
| 2003/0167623 | A1 | 9/2003 | Lorenz |
| 2003/0212308 | A1 | 11/2003 | Bendall |
| 2004/0015053 | A1 | 1/2004 | Bieger |
| 2004/0152972 | A1 | 8/2004 | Hunter |
| 2004/0243147 | A1 | 12/2004 | Lipow |
| 2004/0254566 | A1 | 12/2004 | Plicchi |
| 2005/0004579 | A1 | 1/2005 | Schneider et al. |
| 2005/0177026 | A1 | 8/2005 | Hoeg et al. |
| 2005/0183532 | A1 | 8/2005 | Najaf et al. |
| 2005/0222554 | A1 | 10/2005 | Wallace et al. |
| 2006/0041245 | A1 | 2/2006 | Ferry |
| 2006/0111692 | A1 | 5/2006 | Hlavka et al. |
| 2006/0146010 | A1 | 7/2006 | Schneider |
| 2006/0201688 | A1 | 9/2006 | Jenner et al. |
| 2006/0229587 | A1 | 10/2006 | Beyar et al. |
| 2006/0237205 | A1 | 10/2006 | Sia et al. |
| 2007/0000498 | A1 | 1/2007 | Glynn et al. |
| 2007/0013336 | A1 | 1/2007 | Nowlin et al. |
| 2007/0060879 | A1 | 3/2007 | Weitzner et al. |
| 2007/0100201 | A1 | 5/2007 | Komiva et al. |
| 2007/0100254 | A1 | 5/2007 | Murakami |
| 2007/0112355 | A1 | 5/2007 | Salahich |
| 2007/0119274 | A1 | 5/2007 | Devengenzo et al. |
| 2007/0149946 | A1 | 6/2007 | Viswanathan |
| 2007/0185485 | A1 | 8/2007 | Hauck et al. |
| 2007/0191177 | A1 | 8/2007 | Nagai et al. |
| 2007/0239028 | A1 | 10/2007 | Houser |
| 2007/0245175 | A1 | 10/2007 | Zheng et al. |
| 2007/0299427 | A1 | 12/2007 | Yeung et al. |
| 2008/0039255 | A1 | 2/2008 | Jinno et al. |
| 2008/0046122 | A1 | 2/2008 | Manzo et al. |
| 2008/0065103 | A1 | 3/2008 | Cooper et al. |
| 2008/0147011 | A1 | 6/2008 | Urmey |
| 2008/0177285 | A1 | 7/2008 | Brock et al. |
| 2008/0214925 | A1 | 9/2008 | Wilson et al. |
| 2008/0243064 | A1 | 10/2008 | Stahler et al. |
| 2008/0245175 | A1* | 10/2008 | Jinno .................... A61B 34/72 74/490.01 |
| 2008/0249536 | A1 | 10/2008 | Stahler et al. |
| 2008/0253108 | A1 | 10/2008 | Yu et al. |
| 2008/0262301 | A1 | 10/2008 | Gibbons et al. |
| 2008/0287963 | A1 | 11/2008 | Rogers et al. |
| 2008/0302200 | A1 | 12/2008 | Tobey |
| 2009/0005768 | A1 | 1/2009 | Sharareh |
| 2009/0082722 | A1 | 3/2009 | Munger et al. |
| 2009/0098971 | A1 | 4/2009 | Ho et al. |
| 2009/0105645 | A1 | 4/2009 | Kidd et al. |
| 2009/0163948 | A1 | 6/2009 | Sunaoshi |
| 2009/0171371 | A1 | 7/2009 | Nixon |
| 2009/0247944 | A1 | 10/2009 | Kirschenman et al. |
| 2009/0248039 | A1 | 10/2009 | Cooper et al. |
| 2010/0030023 | A1 | 2/2010 | Yoshie |
| 2010/0069833 | A1 | 3/2010 | Wenderow et al. |
| 2010/0073150 | A1 | 3/2010 | Olson et al. |
| 2010/0082041 | A1 | 4/2010 | Prisco |
| 2010/0130923 | A1 | 5/2010 | Cleary et al. |
| 2010/0130987 | A1 | 5/2010 | Wenderow et al. |
| 2010/0175701 | A1 | 7/2010 | Reis et al. |
| 2010/0204646 | A1 | 8/2010 | Plicchi et al. |
| 2010/0210923 | A1 | 8/2010 | Li et al. |
| 2010/0248177 | A1 | 9/2010 | Mangelberger et al. |
| 2010/0249506 | A1 | 9/2010 | Prisco et al. |
| 2010/0274078 | A1 | 10/2010 | Kim et al. |
| 2010/0332033 | A1 | 12/2010 | Diolaiti |
| 2011/0015484 | A1 | 1/2011 | Alvarez et al. |
| 2011/0015648 | A1 | 1/2011 | Alvarez et al. |
| 2011/0015650 | A1 | 1/2011 | Choi et al. |
| 2011/0028991 | A1 | 2/2011 | Ikeda et al. |
| 2011/0130718 | A1 | 6/2011 | Kidd et al. |
| 2011/0147030 | A1 | 6/2011 | Blum et al. |
| 2011/0152880 | A1 | 6/2011 | Alvarez et al. |
| 2011/0238083 | A1 | 9/2011 | Moll et al. |
| 2011/0261183 | A1 | 10/2011 | Ma et al. |
| 2011/0277775 | A1 | 11/2011 | Holop et al. |
| 2011/0288573 | A1 | 11/2011 | Yates et al. |
| 2011/0306836 | A1 | 12/2011 | Ohline et al. |
| 2012/0071821 | A1 | 3/2012 | Yu |
| 2012/0071894 | A1 | 3/2012 | Tanner et al. |
| 2012/0071895 | A1 | 3/2012 | Stahler et al. |
| 2012/0132018 | A1 | 5/2012 | Tang |
| 2012/0143226 | A1 | 6/2012 | Belson et al. |
| 2012/0150154 | A1 | 6/2012 | Brisson et al. |
| 2012/0186194 | A1 | 7/2012 | Schlieper |
| 2012/0191107 | A1 | 7/2012 | Tanner et al. |
| 2012/0232476 | A1 | 9/2012 | Bhat et al. |
| 2012/0239012 | A1 | 9/2012 | Laurent et al. |
| 2012/0277730 | A1 | 11/2012 | Salahich |
| 2012/0283747 | A1 | 11/2012 | Popovic |
| 2013/0018400 | A1 | 1/2013 | Milton et al. |
| 2013/0066335 | A1 | 3/2013 | Barwinkel |
| 2013/0144116 | A1 | 6/2013 | Cooper et al. |
| 2013/0204124 | A1 | 8/2013 | Duindam |

(56) References Cited

U.S. PATENT DOCUMENTS

| | | | | |
|---|---|---|---|---|
| 2013/0226151 | A1 | 8/2013 | Suehara | |
| 2013/0231678 | A1 | 9/2013 | Wenderow | |
| 2013/0304084 | A1 | 11/2013 | Beira et al. | |
| 2013/0317519 | A1 | 11/2013 | Romo et al. | |
| 2013/0345519 | A1 | 12/2013 | Piskun et al. | |
| 2014/0000411 | A1 | 1/2014 | Shelton, IV et al. | |
| 2014/0066944 | A1 | 3/2014 | Taylor et al. | |
| 2014/0069437 | A1 | 3/2014 | Reis et al. | |
| 2014/0142591 | A1 | 5/2014 | Alvarez et al. | |
| 2014/0166023 | A1 | 6/2014 | Kishi | |
| 2014/0171778 | A1 | 6/2014 | Tsusaka | |
| 2014/0180063 | A1 | 6/2014 | Zhao | |
| 2014/0222019 | A1 | 8/2014 | Brudnick | |
| 2014/0243849 | A1 | 8/2014 | Saglam et al. | |
| 2014/0276233 | A1 | 9/2014 | Murphy | |
| 2014/0276389 | A1 | 9/2014 | Walker | |
| 2014/0276394 | A1 | 9/2014 | Wong et al. | |
| 2014/0276594 | A1 | 9/2014 | Tanner et al. | |
| 2014/0276935 | A1 | 9/2014 | Yu | |
| 2014/0276936 | A1 | 9/2014 | Kokish et al. | |
| 2014/0277334 | A1 | 9/2014 | Yu et al. | |
| 2014/0318288 | A1* | 10/2014 | Lee .................... | A61B 17/2909 74/25 |
| 2014/0357984 | A1 | 12/2014 | Wallace et al. | |
| 2014/0375784 | A1 | 12/2014 | Massetti | |
| 2015/0012134 | A1 | 1/2015 | Robinson | |
| 2015/0090063 | A1 | 4/2015 | Lantermann et al. | |
| 2015/0133963 | A1 | 5/2015 | Barbagli | |
| 2015/0142013 | A1 | 5/2015 | Tanner et al. | |
| 2015/0144514 | A1 | 5/2015 | Brennan et al. | |
| 2015/0148600 | A1 | 5/2015 | Ashinuma et al. | |
| 2015/0150635 | A1 | 6/2015 | Kilroy | |
| 2015/0182250 | A1 | 7/2015 | Conlon et al. | |
| 2015/0231364 | A1 | 8/2015 | Blanchard | |
| 2015/0374445 | A1 | 12/2015 | Gombert et al. | |
| 2016/0000512 | A1 | 1/2016 | Gombert et al. | |
| 2016/0001038 | A1 | 1/2016 | Romo et al. | |
| 2016/0157945 | A1 | 6/2016 | Madhani | |
| 2016/0166234 | A1 | 6/2016 | Zhang | |
| 2016/0192860 | A1 | 7/2016 | Allenby | |
| 2016/0206389 | A1 | 7/2016 | Miller | |
| 2016/0213435 | A1 | 7/2016 | Hourtash | |
| 2016/0270865 | A1 | 9/2016 | Landey et al. | |
| 2016/0287279 | A1 | 10/2016 | Bovay et al. | |
| 2016/0338783 | A1 | 11/2016 | Romo et al. | |
| 2016/0338785 | A1 | 11/2016 | Kokish et al. | |
| 2016/0346049 | A1 | 12/2016 | Allen et al. | |
| 2017/0007337 | A1 | 1/2017 | Dan | |
| 2017/0007343 | A1 | 1/2017 | Yu | |
| 2017/0151028 | A1 | 6/2017 | Ogawa et al. | |
| 2017/0202627 | A1 | 7/2017 | Sramek et al. | |
| 2017/0209073 | A1 | 7/2017 | Sramek et al. | |
| 2017/0258534 | A1 | 9/2017 | Hourtash | |
| 2017/0281049 | A1 | 10/2017 | Yamamoto | |
| 2017/0290631 | A1 | 10/2017 | Lee et al. | |
| 2017/0325932 | A1 | 11/2017 | Hoelzle | |
| 2018/0025666 | A1 | 1/2018 | Ho et al. | |
| 2018/0042464 | A1 | 2/2018 | Arai | |
| 2018/0042686 | A1 | 2/2018 | Peine | |
| 2018/0049792 | A1 | 2/2018 | Eckert | |
| 2018/0056044 | A1 | 3/2018 | Choi et al. | |
| 2018/0104820 | A1 | 4/2018 | Trov et al. | |
| 2018/0116735 | A1 | 5/2018 | Tierney et al. | |
| 2018/0206927 | A1 | 7/2018 | Prisco et al. | |
| 2018/0214011 | A1 | 8/2018 | Graetzel et al. | |
| 2018/0221038 | A1 | 8/2018 | Noonan et al. | |
| 2018/0221039 | A1 | 8/2018 | Shah | |
| 2018/0243048 | A1 | 8/2018 | Shan | |
| 2018/0271616 | A1 | 9/2018 | Schuh et al. | |
| 2018/0279852 | A1 | 10/2018 | Rafii-Tari et al. | |
| 2018/0280660 | A1 | 10/2018 | Landey et al. | |
| 2018/0289431 | A1 | 10/2018 | Draper et al. | |
| 2018/0296299 | A1 | 10/2018 | Iceman | |
| 2018/0303566 | A1 | 10/2018 | Soundararajan | |
| 2018/0325499 | A1 | 11/2018 | Landey et al. | |
| 2018/0326181 | A1 | 11/2018 | Kokish et al. | |
| 2018/0360435 | A1 | 12/2018 | Romo | |
| 2019/0000559 | A1 | 1/2019 | Berman et al. | |
| 2019/0000560 | A1 | 1/2019 | Berman et al. | |
| 2019/0000576 | A1 | 1/2019 | Mintz et al. | |
| 2019/0110839 | A1 | 4/2019 | Rafii-Tari et al. | |
| 2019/0142537 | A1 | 5/2019 | Covington et al. | |
| 2019/0151148 | A1 | 5/2019 | Alvarez et al. | |
| 2019/0167366 | A1 | 6/2019 | Ummalaneni | |
| 2019/0175009 | A1 | 6/2019 | Mintz | |
| 2019/0175062 | A1 | 6/2019 | Rafii-Tari et al. | |
| 2019/0175799 | A1 | 6/2019 | Hsu | |
| 2019/0183585 | A1 | 6/2019 | Rafii-Tari et al. | |
| 2019/0183587 | A1 | 6/2019 | Rafii-Tari et al. | |
| 2019/0216548 | A1 | 7/2019 | Ummalaneni | |
| 2019/0216576 | A1 | 7/2019 | Evre | |
| 2019/0223967 | A1 | 7/2019 | Abbott | |
| 2019/0223974 | A1 | 7/2019 | Romo | |
| 2019/0228525 | A1 | 7/2019 | Mintz et al. | |
| 2019/0231458 | A1 | 8/2019 | DiMaio | |
| 2019/0246882 | A1 | 8/2019 | Graetzel et al. | |
| 2019/0262086 | A1 | 8/2019 | Connolly et al. | |
| 2019/0269468 | A1 | 9/2019 | Hsu et al. | |
| 2019/0274764 | A1 | 9/2019 | Romo | |
| 2019/0290109 | A1 | 9/2019 | Agrawal et al. | |
| 2019/0298160 | A1 | 10/2019 | Ummalaneni et al. | |
| 2019/0298460 | A1 | 10/2019 | Al-Jadda | |
| 2019/0298465 | A1 | 10/2019 | Chin | |
| 2019/0336238 | A1 | 11/2019 | Yu | |
| 2019/0365201 | A1 | 12/2019 | Noonan et al. | |
| 2019/0365209 | A1 | 12/2019 | Ye et al. | |
| 2019/0365479 | A1 | 12/2019 | Rafii-Tari | |
| 2019/0365486 | A1 | 12/2019 | Srinivasan et al. | |
| 2019/0374297 | A1 | 12/2019 | Wallace et al. | |
| 2019/0375383 | A1 | 12/2019 | Alvarez | |
| 2019/0380787 | A1 | 12/2019 | Ye | |
| 2019/0380797 | A1 | 12/2019 | Yu | |
| 2020/0000533 | A1 | 1/2020 | Schuh | |
| 2020/0008874 | A1 | 1/2020 | Barbagli et al. | |
| 2020/0022767 | A1 | 1/2020 | Hill | |
| 2020/0038123 | A1 | 2/2020 | Graetzel | |
| 2020/0039086 | A1 | 2/2020 | Meyer | |
| 2020/0046434 | A1 | 2/2020 | Graetzel | |
| 2020/0054408 | A1 | 2/2020 | Schuh et al. | |
| 2020/0060516 | A1 | 2/2020 | Baez | |
| 2020/0085516 | A1 | 3/2020 | DeFonzo | |
| 2020/0086087 | A1 | 3/2020 | Hart et al. | |
| 2020/0091799 | A1 | 3/2020 | Covington et al. | |
| 2020/0093549 | A1 | 3/2020 | Chin | |
| 2020/0093554 | A1 | 3/2020 | Schuh | |
| 2020/0100845 | A1 | 4/2020 | Julian | |
| 2020/0100853 | A1 | 4/2020 | Ho | |
| 2020/0100855 | A1 | 4/2020 | Leparmentier | |
| 2020/0101264 | A1 | 4/2020 | Jiang | |
| 2020/0107894 | A1 | 4/2020 | Wallace | |
| 2020/0121502 | A1 | 4/2020 | Kintz | |
| 2020/0129252 | A1 | 4/2020 | Kokish | |
| 2020/0146769 | A1 | 5/2020 | Evre | |
| 2020/0155245 | A1 | 5/2020 | Yu | |
| 2020/0155801 | A1 | 5/2020 | Kokish | |
| 2020/0170720 | A1 | 6/2020 | Ummalaneni | |
| 2020/0171660 | A1 | 6/2020 | Ho | |
| 2020/0188043 | A1 | 6/2020 | Yu | |
| 2020/0197112 | A1 | 6/2020 | Chin | |
| 2020/0206472 | A1 | 7/2020 | Ma | |
| 2020/0217733 | A1 | 7/2020 | Lin | |
| 2020/0222134 | A1 | 7/2020 | Schuh | |
| 2020/0230360 | A1 | 7/2020 | Yu | |
| 2020/0237458 | A1 | 7/2020 | DeFonzo | |
| 2020/0261172 | A1 | 8/2020 | Romo | |
| 2020/0268459 | A1 | 8/2020 | Noonan et al. | |
| 2020/0268460 | A1 | 8/2020 | Tse | |
| 2020/0281787 | A1 | 9/2020 | Ruiz | |
| 2020/0297437 | A1 | 9/2020 | Schuh | |
| 2020/0305983 | A1 | 10/2020 | Yampolsky | |
| 2020/0305989 | A1 | 10/2020 | Schuh | |

(56) References Cited

U.S. PATENT DOCUMENTS

| | | | |
|---|---|---|---|
| 2020/0315717 A1 | 10/2020 | Bovay | |
| 2020/0315723 A1 | 10/2020 | Hassan | |

FOREIGN PATENT DOCUMENTS

| | | |
|---|---|---|
| CN | 201884596 U | 6/2011 |
| CN | 102316817 | 1/2012 |
| CN | 102327118 | 1/2012 |
| CN | 102458295 | 5/2012 |
| CN | 102665590 | 9/2012 |
| CN | 102834043 | 12/2012 |
| CN | 102973317 | 3/2013 |
| CN | 102015759 | 4/2013 |
| CN | 103735313 | 4/2014 |
| CN | 105147393 | 12/2015 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| JP | 2014-159071 | 9/2014 |
| JP | 2014193417 A | 10/2014 |
| KR | 20140037119 A | 3/2014 |
| WO | WO 02/74178 | 9/2002 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/151993 | 9/2017 |

OTHER PUBLICATIONS

Korean Office Action; Application No. 10-2023-7021100; Nov. 9, 2023; 12 pages.

Mayo Clinic, Robotic Surgery, https://www.mayoclinic.org/tests-procedures/robotic-surgery/about/pac-20394974?p=1, downloaded from the internet on Jul. 12, 2018, 2 pp.

Extended European Search Report dated Mar. 30, 2020 in patent application No. 1691538.4.

International Search Report and Written Opinion dated Nov. 21, 2016 in PCT/US16/49775.

* cited by examiner

LENGTH CONSERVATIVE SURGICAL INSTRUMENT

CROSS REFERENCE TO RELATED APPLICATIONS

This application is a continuation of U.S. application Ser. No. 16/900,009, filed on Jun. 12, 2020, now U.S. Pat. No. 11,564,759, issued on Jan. 31, 2023, which is a continuation of U.S. application Ser. No. 15/970,750, filed on May 3, 2018, now U.S. Pat. No. 10,682,189, issued on Jun. 16, 2020, which is a continuation of U.S. application Ser. No. 15/353,576, filed on Nov. 16, 2016, now U.S. Pat. No. 9,962,228, issued on May 8, 2018, which is a continuation of PCT Application No. PCT/US2016/049775, filed on Aug. 31, 2016, all of which are incorporated by reference herein in their entirety.

BACKGROUND

Field of Art

This description generally relates to surgical robotics, and particularly to a surgical wrist with active tensioning.

Description of the Related Art

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments such as laparoscopes.

Laparoscopes with movable tips help perform surgical procedures in a minimally invasive manner. A movable tip can be directed through the abdominal wall to a more remote location of a patient, such as the intestines or stomach. The movable tips in a robotically controlled laparoscope have several degrees of freedom that mimic a surgeon's wrist in traditional surgical operations. These movable tips, also referred as a robotic wrist or simply as a wrist, have evolved with technology and encompass a variety of technologies for creating motion about as many degrees of freedom as possible while using a minimal number of motors the surgical instrument.

Many such robotic wrists use a pre-tensioned loop of cable. This allows for the instrument to be driven with a minimum of motors relative to instruments that are tensioned with a motor for each cable. Such a "closed loop" cabling system makes it more difficult to map motor torque to cable tension. This is partly because of the preload in the system and partly due to the frictions the preload causes. End of life for a pre-tensioned instrument is usually because the cables loose tension over time due to a combination of mechanical wear, effects of cleaning chemicals, and stretch of the cables.

SUMMARY

This description relates to a robotic surgical wrist with three degrees of freedom (DOF) that maintains the length and tension of the cables that control those DOF throughout the surgical operation.

The surgical robotic system controlling the wrist uses a master/slave system in which a master device controls motion of a slave device at a remote location. Generally, the slave device is a robotic surgical instrument that approximates a classical surgical tool for a surgical operation, e.g. a forceps in a laparoscopy.

In one embodiment, the slave surgical instrument has a surgical effector for performing surgical operations at a surgical site with three degrees of freedom in motion, a pitch angle, a first yaw angle, and a second yaw angle. Additionally, the surgical effector has a 'fourth degree of freedom' which is a measure of the relative yaw angles and the tension of their respective cables in the surgical effector. The surgical effector also a translation degree of freedom along an operation axis controlled by an external arm and a rotation degree of freedom about the operation axis controlled by an external instrument device manipulator.

To control the degrees of freedom of the surgical effector the surgical instrument has a set of four input controllers, four cables, a reciprocal pantograph, a cable shaft, and a surgical effector. Two of the cables couple two pairs of input controllers via the surgical effector such that their actuation, e.g. spooling or unspooling, manipulates the length of the cable's segment to create motion of the surgical effector about the degrees of freedom. The other two cables couple the two pairs of input controllers to the reciprocal pantograph such that the actuation creating motion of the surgical effectors creates a reciprocal motion in the reciprocal pantograph. The reciprocal pantograph maintains a constant length of cable between each pair of input controllers by rotating the reciprocal pantograph.

The surgical wrist may be controlled by a computer program designed to interpret motions of a user into surgical operations at the surgical site. This computer program interprets user motion and creates a set of instructions for appropriately manipulating the four cables via spooling and unspooling the input controllers to translate the user motion to motion of the surgical effector.

BRIEF DESCRIPTION OF DRAWINGS

The disclosed embodiments have other advantages and features which will be more readily apparent from the following detailed description of the invention and the appended claims, when taken in conjunction with the accompanying drawings, in which:

DETAILED DESCRIPTION

I. Surgical Robotic Systems

Figure 1:
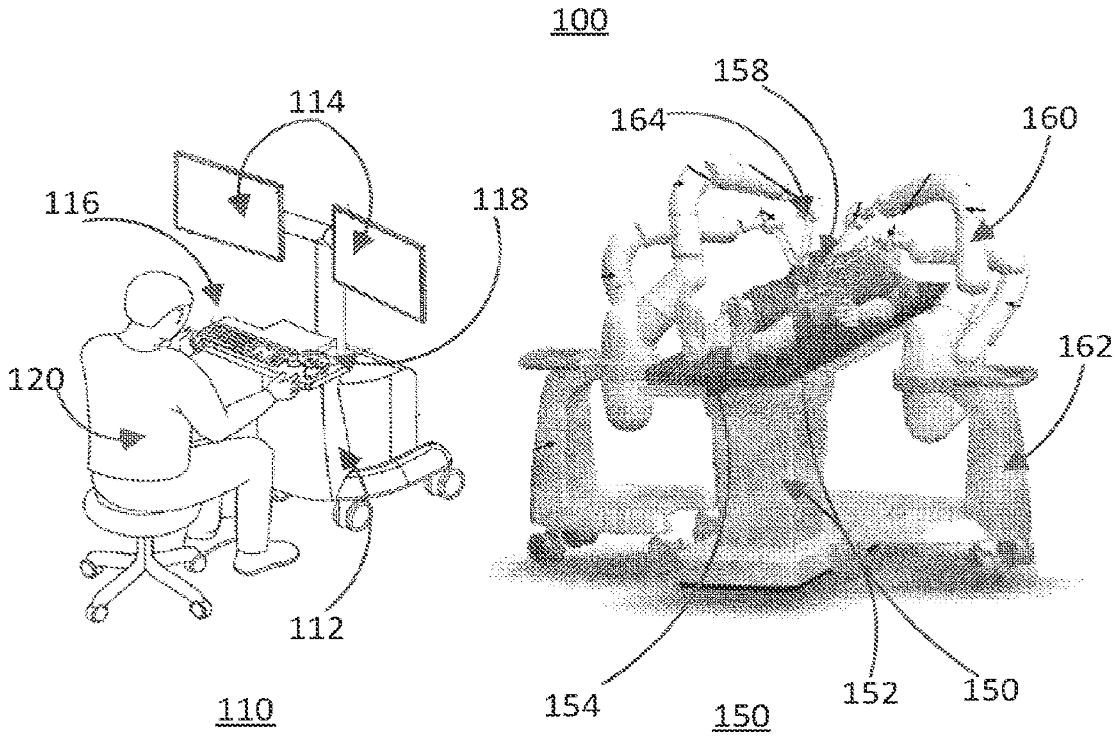
FIG. 1 illustrates an example representation of a surgical robotic system.

FIG. 1 illustrates an example representation of a master/slave surgical robotic system 100 consisting of a master device 110 and a slave device 150. Generally, the master device is a command console for a surgical robotic system 100. The master device 110 includes a console base 112, display modules 114, e.g., monitors, and control modules, e.g., a keyboard 116 and joystick 118. In some embodiments, one or more of the master device 110 functionality may be integrated into the slave device 150 of the surgical robotic system 100 or another system communicatively coupled to the surgical robotic system 100. A user 120, e.g., a physician, remotely controls the surgical robotic system 100 from an ergonomic position using the master device 110.

The slave device 150 has a table base 152 to support a surgical table 154 upon which a patient 156 is positioned for a surgical procedure at a surgical site 158. At least one robotic arm 160 mounted to at least one locatable base 162 for manipulating surgical effectors 164, is positioned in close proximity to the table base 152 and the surgical table 154. Rather than having an independent and movable locatable base 162, the robotic arms 160 may be coupled to the table base 152. The table base 152 and the surgical table 154 may include motors, actuators, or other mechanical or electrical means for changing the orientation of the surgical table. In some embodiments the table base 152 and the surgical table 154 may be configured to change the orientation of the patient 156 and the surgical table for different types of surgical procedures at different surgical sites.

The slave device 150 may include a central processing unit, a memory unit, a data bus, and associated data communication ports that are responsible for interpreting and processing signals such as camera imagery and tracking sensor data, e.g., from the robotic manipulators. The console base 112 may include a central processing unit, a memory unit, a data bus, and associated data communication ports that are responsible for interpreting and processing signals such as camera imagery and tracking sensor data, e.g., from the slave device. In some embodiments, both the console base 112 and the slave device 150 perform signal processing for load-balancing.

The console base 112 may also process commands and instructions provided by the user 120 through the control modules 116 and 118. In addition to the keyboard 116 and joystick 118 shown in FIG. 1, the control modules may include other devices, for example, computer mice, trackpads, trackballs, control pads, video game controllers, and sensors (e.g., motion sensors or cameras) that capture hand gestures and finger gestures.

The user 120 can control a surgical effector 164 coupled to the slave device 150 using the master device 110 in a velocity mode or position control mode. In velocity mode, the user 120 directly controls pitch and yaw motion of the surgical instrument based on direct manual control using the control modules. For example, movement on the joystick 118 may be mapped to yaw and pitch movement of the surgical effectors 164. The joystick 118 can provide haptic feedback to the user 120. For example, the joystick 118 vibrates to indicate that the surgical effectors 164 cannot further translate or rotate in a certain direction. The command console 112 can also provide visual feedback (e.g., pop-up messages) and/or audio feedback (e.g., beeping) to indicate that the surgical effectors 164 have reached maximum translation or rotation.

In position control mode, the command console 112 uses a three-dimensional (3D) map of a patient and pre-determined computer models of the patient to control the slave device 150. The command console 112 provides control signals to robotic arms 160 of the surgical robotic system 100 to manipulate the surgical effectors to the surgical site 158. Due to the reliance on the 3D map, position control mode requires accurate mapping of the anatomy of the patient.

In some embodiments, users 120 can manually manipulate robotic arms 160 of the surgical robotic system 100 without using the master device 110. During setup in a surgical operating room, the users 120 may move the robotic arms 160, surgical effectors 164, and other surgical equipment to access a patient. The surgical robotic system 100 may rely on force feedback and inertia control from the users 120 to determine appropriate configuration of the robotic arms 160 and equipment.

The display modules 114 may include electronic monitors, virtual reality viewing devices, e.g., goggles or glasses, and/or other means of display devices. In some embodiments, the display modules 114 are integrated with the control modules, for example, as a tablet device with a touchscreen. Further, the user 120 can both view data and input commands to the surgical robotic system 100 using the integrated display modules 114 and control modules.

The display modules 114 can display 3D images using a stereoscopic device, e.g., a visor or goggle. The 3D images provide a "surgical view," which is a computer 3D model illustrating the anatomy of a patient at the surgical site 158. The "surgical view" provides a virtual environment of the patient's interior and an expected location of the surgical effectors 164 inside the patient. A user 120 compares the "surgical view" model to actual images captured by a camera to help mentally orient and confirm that the surgical effectors 164 are in the correct—or approximately correct—location within the patient. The "surgical view" provides information about anatomical structures, e.g., the shape of an intestine or colon of the patient, around the surgical site. The display modules 114 can simultaneously display the 3D model and computerized tomography (CT) scans of the anatomy at the surgical site. Further, the display modules 114 may overlay pre-determined optimal navigation paths of the surgical effectors 164 on the 3D model and CT scans.

In some embodiments, a model of the surgical effectors is displayed with the 3D models to help indicate a status of a surgical procedure. For example, scans identify a region in the anatomy where a suture may be necessary. During operation, the display modules 114 may show a reference image captured by the surgical effectors 164 corresponding to the current location of the surgical effectors at the surgical site 158. The display modules 202 may automatically display different views of the model of the endoscope depending on user settings and a particular surgical procedure. For example, the display modules 202 show an overhead fluoroscopic view of the surgical end effector during a navigation step as the surgical end effector approaches an operative region of a patient.

II. Slave Robotic Device

Figure 2:
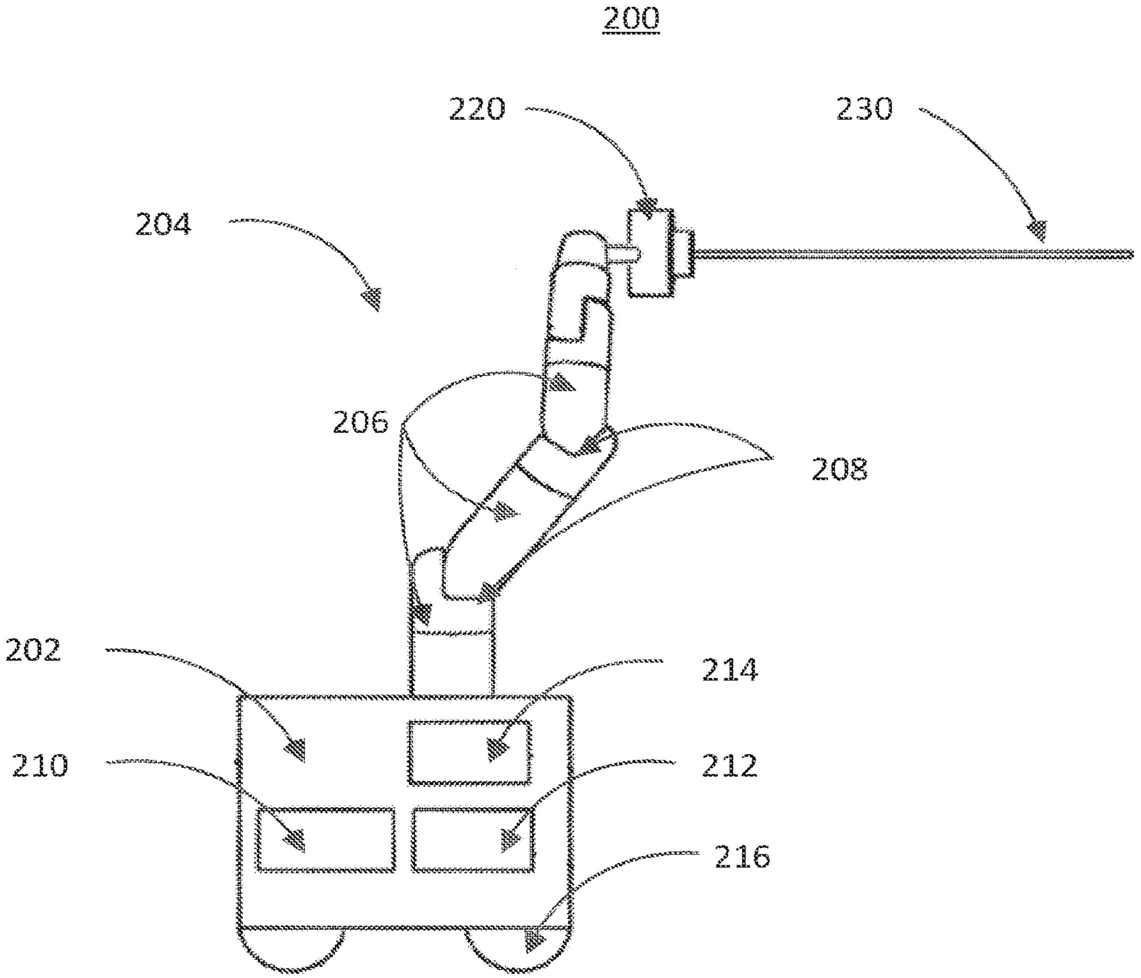
FIG. 2 illustrates an example representation of a slave device in a master/slave surgical robotic system.

FIG. 2 illustrates a slave robotic device 200 from a surgical robotic system 100 according to one embodiment. The slave device 200 includes a slave base 202 coupled to one or more robotic arms, e.g., robotic arm 204. The slave base 202 is communicatively coupled to the master device 110. The slave base 202 can be positioned such that the robotic arm 204 has access to perform a surgical procedure on a patient, while a user such as a physician may control the surgical robotic system 100 from the master device. In some embodiments, the slave base 202 may be coupled to a surgical operating table for supporting the patient. Though not shown in FIG. 1 for purposes of clarity, the slave base 202 may include subsystems such as control electronics, pneumatics, power sources, optical sources, and the like. The robotic arm 204 includes multiple arm segments 206 coupled at joints 208, which provides the robotic arm 202 multiple degrees of freedom. The slave base 202 may contain a source of power 210, pneumatic pressure 212, and control and sensor electronics 214—including components such as a central processing unit, data bus, control circuitry, and memory—and related actuators such as motors to move the robotic arm 204. The electronics 214 in the slave base 202 may also process and transmit control signals communicated from the command console.

In some embodiments, the slave base 202 includes wheels 216 to transport the slave robotic device 150. Mobility of the slave robotic device 150 helps accommodate space constraints in a surgical operating room as well as facilitate appropriate positioning and movement of surgical equipment. Further, the mobility allows the robotic arms 204 to be configured such that the robotic arms 204 do not interfere with the patient, physician, anesthesiologist, or any other equipment. During procedures, a user may control the robotic arms 204 using control devices such as the master device.

In some embodiments, the robotic arm 204 includes set up joints that use a combination of brakes and counter-balances to maintain a position of the robotic arm 204. The counter-balances may include gas springs or coil springs. The brakes, e.g., fail safe brakes, may be include mechanical and/or electrical components. Further, the robotic arms 204 may be gravity-assisted passive support type robotic arms.

The robotic arm may be coupled to a surgical instrument, e.g. a laparoscope 220, with the robotic arm positioning the surgical instrument at a surgical site. The robotic arm may be coupled to the surgical instrument with a specifically designed connective apparatus 230 that allows communication between the surgical instrument and the base, the base configured to control of the surgical instrument via the robotic arm.

III. Instrument Device Manipulator

Figure 3:
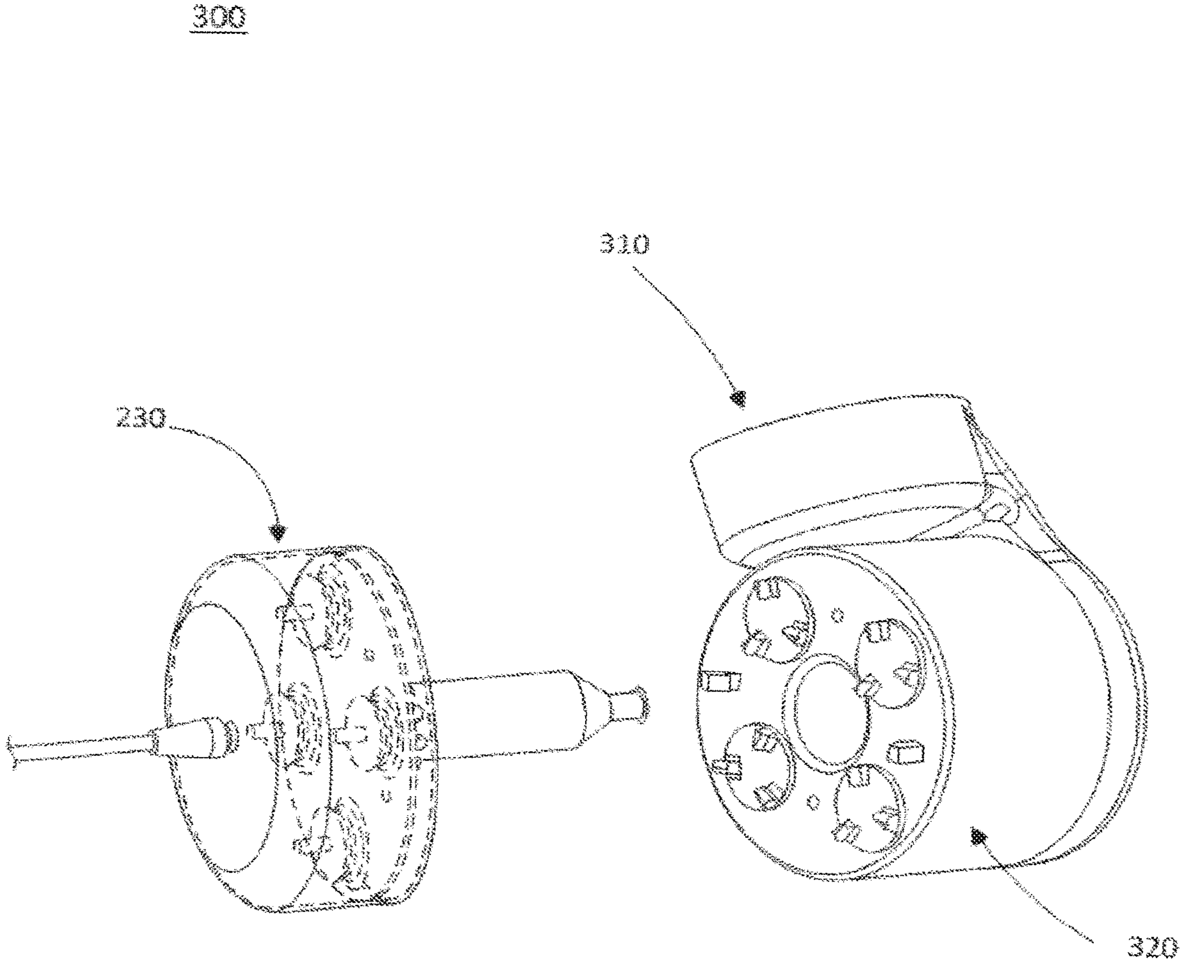
FIG. 3 illustrates an example representation of the end of a robotic arm coupling to a surgical instrument in a master/slave surgical system.

FIG. 3 illustrates an embodiment of the end of a robotic arm 300 in a master/slave surgical system. At the end of each robotic arm, a mechanism changer interface (MCI) 310 may couple an instrument device manipulator (IDM) 320 to the robotic arm. The MCI 310 can be a set screw or base plate connector. The MCI 310 includes connectors to transfer pneumatic pressure, electrical power, electrical signals, and optical signals from the robotic arm to the IDM 320.

The MCI 310 removably or fixedly mounts the IDM 320 to a surgical robotic arm of a surgical robotic system. The IDM is configured to attach the connective apparatus 230 (e.g., via a support bracket and mounting bracket as described in FIG. 4 below) of a surgical tool to a robotic surgical arm in a manner that allows the surgical tool to be continuously rotated or "rolled" about an axis of the surgical tool. The IDM 320 may be used with a variety of surgical tools (not shown in FIG. 3), which may include a housing and an elongated body, and which may be for a laparoscope, an endoscope, or other types of end-effectors of surgical instruments.

IV. Surgical Instrument

Figure 4:
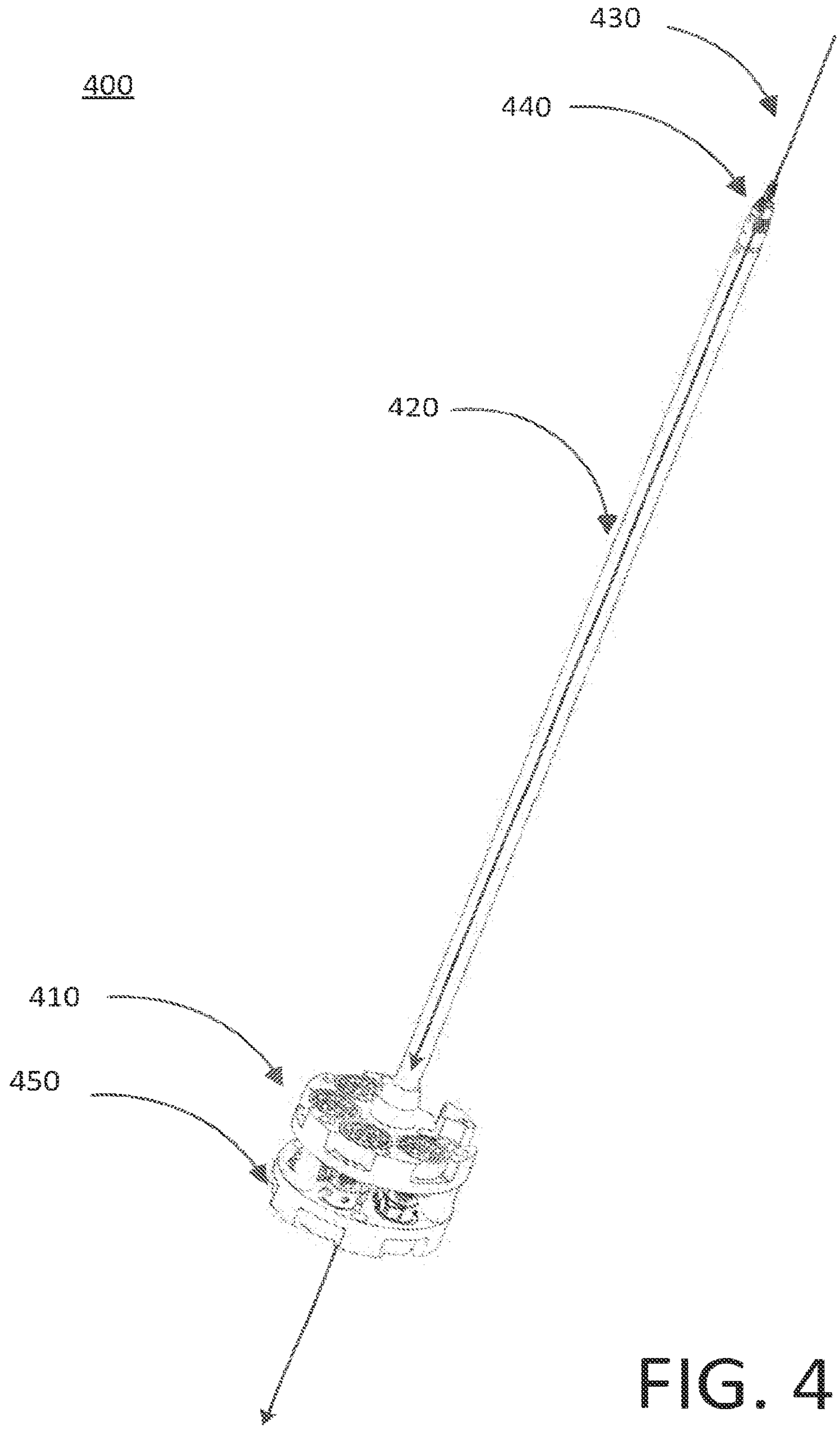
FIG. 4 illustrates an example representation of the surgical instrument in a master/slave surgical system.

FIG. 4 illustrates an example representation of the surgical instrument in a master/slave surgical system 400. The surgical instrument is coupled to the IDM 320 via a support bracket 410 and mounting bracket 450. The support bracket 410 and mounting bracket 450 are disk shaped, with a cable shaft 420 centrally located on the disk of the support bracket and extending outward normal to the plane of the support bracket 410 opposite the mounting bracket 450 along an operation axis 430. The cable shaft 420 couples the surgical effector 440 to the support bracket 410 allowing control of the surgical effector by the slave base via the robotic arm and the IDM.

V. Support Bracket

Figure 5:
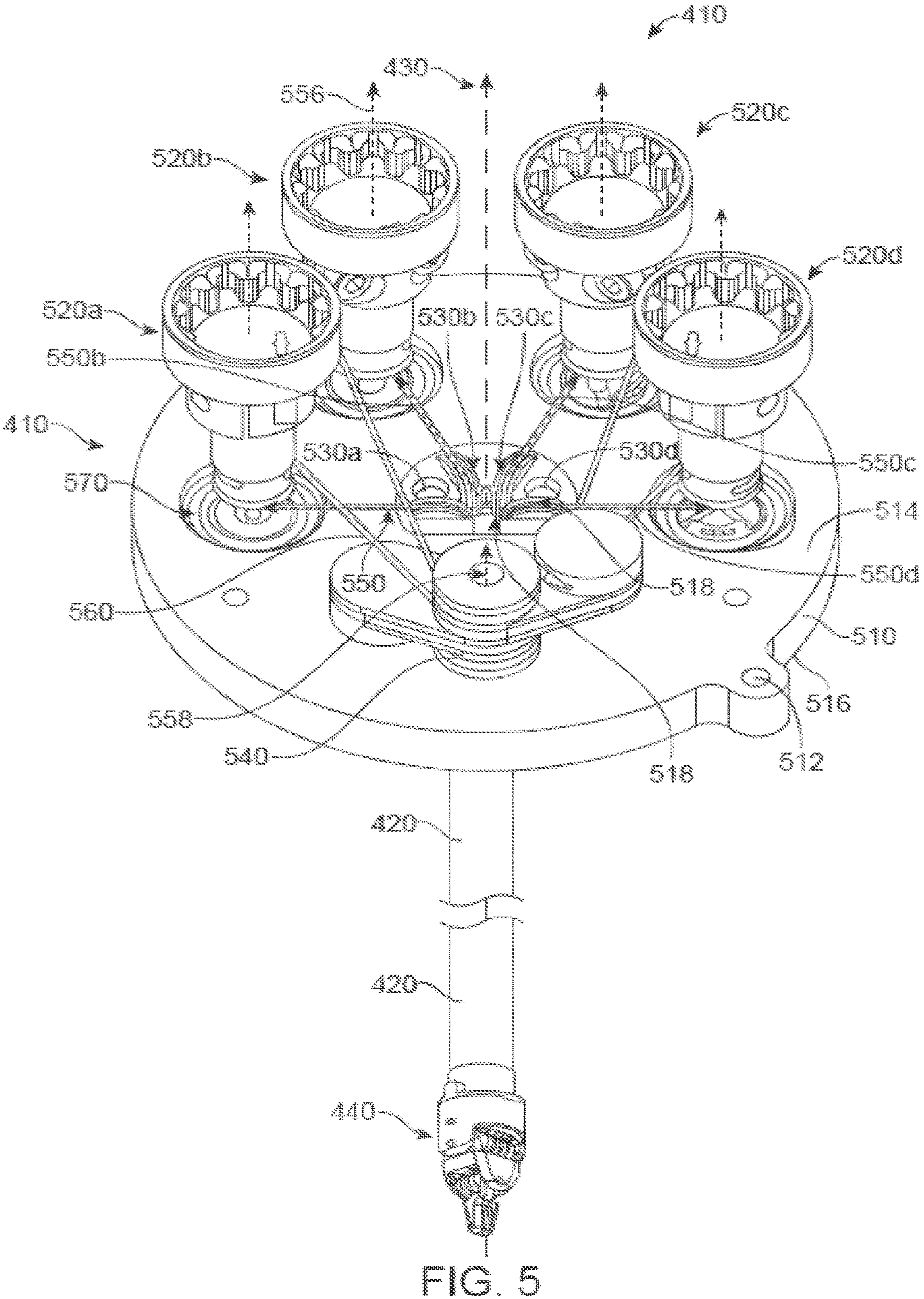
FIG. 5 illustrates an isometric view of an example support bracket demonstrating its constituent components.

FIG. 5 illustrates an isometric view of an embodiment of the support bracket, with the mounting bracket not shown, demonstrating its constituent components. The support bracket 410 includes a support base 510 which is approximately disk shaped with at least one connective through-hole 512 coupled to the outer edge of the disk to assist coupling the support bracket to the mounting bracket. In some embodiments, there is no connective through-hole for coupling the support bracket to the mounting bracket. In other embodiments, there is no mounting bracket and the support bracket directly couples to the IDM. One face of the support base, hereafter the coupling face 514, acts as a support structure for the input controllers 520, the guidance pulleys 530, and the reciprocal pantograph 540. The opposite face of the support base 510, hereafter the operation face 516 (not visibly shown), acts as a support structure for the cable shaft 420.

In the center of the support base is an operative through-hole 518 through the support base 510 from the coupling face 514 to the operation face 516 along the operation axis 430 for coupling the input controllers 520 to the surgical effectors 440 via the cable shaft 420. The operative through-hole 518 has a diameter large enough to allow at least four cable 560 segments to pass unimpeded through the support base 510 from the coupling face 514 to the operation face 516.

Along the outer edge of the operative through-hole are a set of four guidance pulleys 530, two outer 530*a*, 530*d* and two inner 530*b*, 530*c* that are at least partially recessed below the plane of the coupling face. The plane of each guidance pulley 530 is orthogonal to the plane of the coupling face 514, with the plane of a pulley is the plane of pulley's disc. The pulleys are positioned such that the plane of each guidance pulley is normal to the edge of the operative through-hole 518 with at least a portion of the guidance pulley extended into the operative through-hole. The guidance pulleys 530 are coupled to the support base 510 and configured to rotate about a central guidance axis coplanar to the plane of the support base 510. In one embodiment, the guidance pulleys 530 are connected to the support base 510 via bearings. The guidance pulleys allow cables 560 to move through the operative through-hole 518 without tangling with one another or chaffing against the edge of the operative through-hole.

The rays from the operation axis 430 outwards along the plane of the guidance pulleys create a set of four cable axes 550, two outer axes 550*a*, 550*d* and two inner axes 550*b*, 532*c*. The guidance pulleys 530 are positioned such that the outer cable axes 550*a*, 550*d* form a line along the support bracket diameter, the angle between an outer cable axis (e.g. 550*a*) and the nearest inner cable axis (e.g. 550*b*) is a non-zero angle between 0 and 90 degrees, an example of which is illustrated in FIG. 5 as being approximately 60 degrees. Similarly, the angle between two inner cable axes (e.g. 550*b* and 550*c*) is an angle between 0 and 90 degrees, an example of which is illustrated as approximately 60 degrees.

VI. Cable Shaft

The cable shaft 420 couples the surgical effector 440 to the support bracket 410 allowing control of the surgical effector by the slave base via the robotic arm and the IDM. In one embodiment, the cable shaft is a long hollow cylinder with an action end and a driver end, the action end coupling to the surgical effector 440 and the driver end coupling to the operation face 516 of the support bracket 510. The cable shaft is coupled to the support bracket 510 such that the cable shaft 420 extends orthogonally from the support bracket along the operation axis 430. The cable shaft 420 houses the cables 560 which couple the input controllers 520 to the surgical effector 440.

VII. Input Controllers

Two outer input controllers 520*a*, 520*d* and two inner input controllers 520*b*, 520*c* are coupled to the support base and extend orthogonally outwards from the coupling face 514. The input controllers 520 are positioned along a concentric half ring about the operation axis 430 with each input controller radially equidistant from the operation axis along one of the cable axes 550. The input controllers 520 may be a similarly shaped to an inverted tiered cylindrical pyramid, with cylinders of increasing radii coupled atop one another. The coupled cylinders of the input controllers 520 are centrally aligned along a spooling axis 556 associated with that particular input controller that is orthogonal to the coupling face 514 and parallel to the operation axis 430. The input controllers are positioned such that the two spooling axes 556 of the outer input controllers 520*a*, 520*d* form a line along the diameter of the support bracket similarly to the two outer cable axes, and forming similar angles with their closest respective inner input controllers with respect to the operation axis 430 accordingly. The two inner input controllers similarly are located at an angle with respect to each other similarly to the two inner cable axes, as described above.

The support base 510 contains four circularly shaped rotary joints 570. The rotary joints 570 are configured to allow each input controller to rotate about its spooling axis, such as 556. The rotary joints 570 are formed such that the top of each rotary joint is substantially flush to or slightly recessed from the coupling face 514 of the support base 510. The rotary joints 570 are similarly positioned to the input controllers 520 with each input controller coupled to the center of a rotary joint such that the rotation axis of the rotary joint is coaxial with the spooling axis 556 of the associated input controller. In one embodiment, the rotary joint is a bearing.

While not pictured in FIG. 5, the support bracket is further coupled to the mounting bracket 450 via the input controllers. The mounting bracket couples to the input controllers such that the top of the input controllers pass through the mounting bracket and the top of the input controllers are substantially flush with the top of the mounting bracket. The mounting bracket is further configured with a similar set of rotary joints coaxial to the rotary joints of the support bracket which allows the input controllers to rotate. The input controllers 520 and mounting bracket 450 are configured to be coupled to the IDM and actuate the cables 560 to control motion of the surgical effector 440, described in detail in later sections. The cables 560 are coupled to the input controllers 520 such that the cables are at least partially wrapped around the input controllers and may spool or unspool around controllers as they rotate about the spooling axis. Each input controller is coupled to a single cable.

VIII. Reciprocal Pantograph

The reciprocal pantograph 540 is a physical structure containing multiple physical components that is named as such because it is configured to move in a reciprocal manner to the surgical effector, discussed in sections X and XI. Thus, the reciprocal pantograph allows the surgical instrument as a whole, the wrist specifically, and the cables within more specifically, to be length conservative. The cables are tightened using traditional techniques such as a fixed clamp or spooling around a cylinder, which is subject to becoming loose (less tensioned) over time through normal wear and tear. While cable wear may cause a change in the overall length of the cable, this change is compensated for by the IDM, robotic arm, and controlling computer to maintain a length conservative system. The reciprocal pantograph is further configured to maintain the length of the cables in the surgical instrument when not being controlled by the input controllers and IDM, for example when the surgical instrument is detached from the slave surgical device.

The reciprocal pantograph has two modes of operation: attached mode, in which the surgical instrument is attached to the IDM and robotic arm such that the IDM and robotic arm are able to actuate the input controllers and control the motion of the surgical effectors; and detached mode, in which the surgical instrument is detached from the IDM and robotic arm such that the reciprocal pantograph and input controllers passively maintain the length of the surgical cables of the surgical effector, thereby preventing it from coming loose/falling off.

VIII-A. Reciprocal Pantograph Construction

The reciprocal pantograph 540 is coupled to the support base 510 on the half of the coupling face 514 opposite the inner input controllers 524. The reciprocal pantograph 540, shown with an expanded view in FIG. 6, includes two coupled differentials, a rotation shaft, and an armature. The rotation shaft extends orthogonally outward from the coupling face 514 with the central axis of the rotation shaft, hereafter reciprocal axis 558, being parallel to the operation axis 430. The rotation shaft is positioned a radial distance away from the operation axis 430. Additionally, the angle between an outer spooling axis 556, the operation axis 430, and the reciprocal axis 558 is approximately 90 degrees, though in other embodiments it may be at a different angle.

Figure 6A:
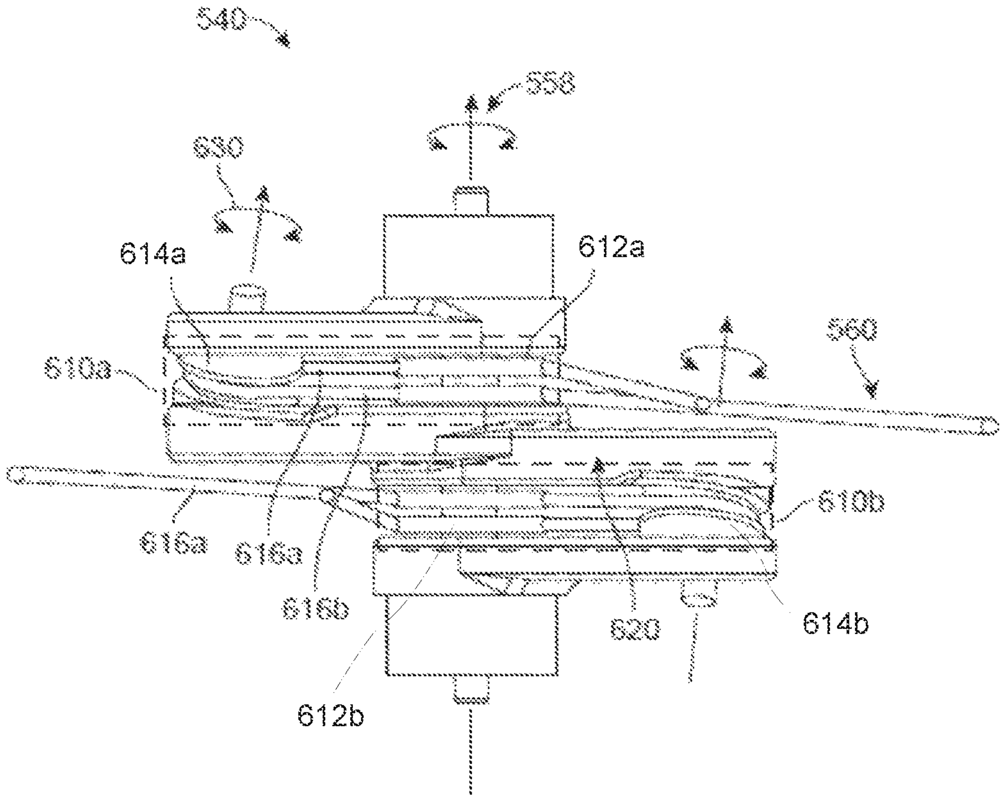
FIG. 6A illustrates an example representation of a reciprocal pantograph of the surgical instrument.

FIG. 6A is an isometric view of the example reciprocal pantograph 540. The reciprocal pantograph consists of an armature 620 coupling two differentials 610*a* and 610*b*. The first differential 610*a* couples of a pair of pulleys, the first pulley being a reciprocal wrist pulley 612*a* with two grooves and the second pulley being a reciprocal member pulley 614*a* with one groove. The second differential 610*b* is similarly constructed with a wrist pulley 612*b* and a member pulley 614*b*. In another embodiment, the reciprocal wrist pulleys 612*a* and 612*b* may comprise two separate coaxial single groove pulleys or a single pulley with a single groove large enough to allow for two cables. The armature 620 couples the differentials 610*a* and 610*b* to each other such that the reciprocal wrist pulleys 612*a* and 612*b* are coaxial to each other and to the reciprocal axis 558. Additionally, the armature 620 couples the reciprocal member pulleys 614*a* and 614*b* of each differential an equal distance from the reciprocal wrist pulleys 612*a* and 612*b*. The armature 620 further couples the reciprocal member pulleys 614*a* and 614*b* such that they are located a non-zero angle apart from each other about the reciprocal axis 558. In other embodiments, the reciprocal member pulleys 612 are a dissimilar distance away from the reciprocal wrist pulleys 614. The reciprocal member pulleys 614 are rotated about a tensile axis 630, the tensile axis forming an acute angle to the reciprocal axis 558.

VIII-B. Reciprocal Pantograph Cabling

Within each differential 610, the reciprocal wrist pulley 612 and reciprocal member pulley 614 are further coupled by a cable 560. For sake of discussion the cable may be described as having an inbound segment 616*a* and an outbound segment 616*b*, with the inbound segment extending from the reciprocal axis 558 towards the tensile axis 630 and the outbound segment extending from the tensile axis toward the reciprocal axis. As the cables move during use, the segment definitions are arbitrary, and are defined here for sake of clarity relative to the pulleys, rather than being at fixed locations on the cables themselves.

On the inbound segment 616*a*, the cable at least partially loops around the reciprocal wrist pulley 612 in its first groove. The cable then at least partially loops around the reciprocal member pulley 614, coupling the reciprocal member pulley to the reciprocal wrist pulley 612 transitioning to the outbound segment. On the outbound segment 616*b*, the cable then further at least partially loops around the reciprocal member pulley 614, thereby reverses the direction of the cable after which it is directed away from the tensile axis 630. The outbound segment of the cable at least partially loops around the second groove of the reciprocal member wrist pulley 612, after which it is directed away from the reciprocal axis 558.

VIII-C. Reciprocal Pantograph Motion

Figure 6B:
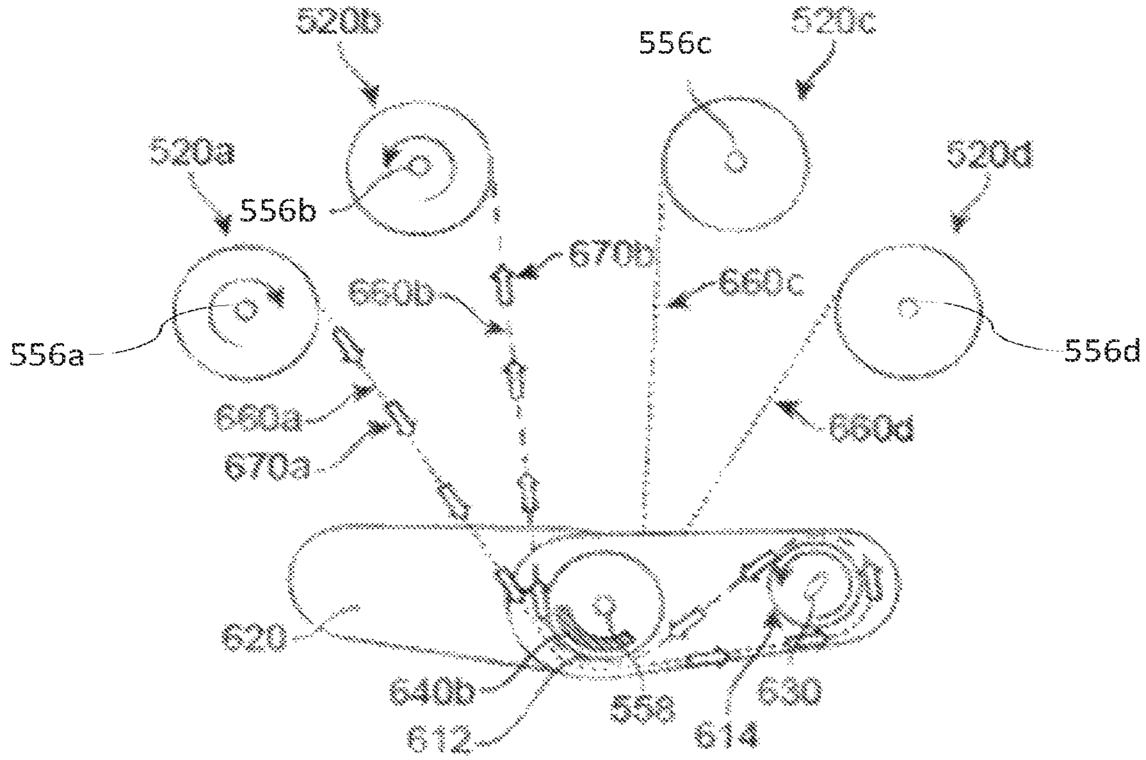
FIG. 6B illustrates an example representation of a tensile state of the reciprocal pantograph of the surgical instrument in a master/slave surgical system.

FIG. 6B illustrates an example of how the input controllers are coupled to the restraint pantograph. The top tier of each input controller 520, i.e. the cylinder furthest removed from the coupling face of the support bracket, is configured to removably attach the input controller to a corresponding actuator of the IDM such that the IDM can manipulate the rotation of the input controller about their independent spooling axes 556*a* 556*b* 556*c*, 556*d*. Additionally, each pair of input controllers 520 is coupled to one of the differentials 610 of the reciprocal pantograph 540 by a cable 560 such that the inbound segment and outbound segment of the cable couples the first input controller to the second input controller of an input controller pair. In the illustrated embodiment, an outer 520*a* and an inner 520*b* input controller are paired by a first cable and the inner 520*c* and outer 520*d* are paired by a second cable, but one knowledgeable in the art will recognize that any two input controllers may be paired together.

While the laparoscopic tool is attached to the IDM to perform operations at the surgical site, the reciprocal pantograph is in attached mode. While in attached mode, the differentials of the reciprocal pantograph maintain a constant length in each of the cables coupling each pair of input controllers. The total length in a cable is manipulated by the interplay of spooling and unspooling the pair of input controllers associated with a given cable, as well as by the rotation of the restraint pantograph about the reciprocal axis. To maintain the length of the cables, the pulleys in the differentials and the armature rotate about the reciprocal and tensile axes to create an equal and opposite lengthening (or shortening) to compensate for the shortening (or lengthening) created by spooling or unspooling input controllers about their spooling axes.

Figure 6C:
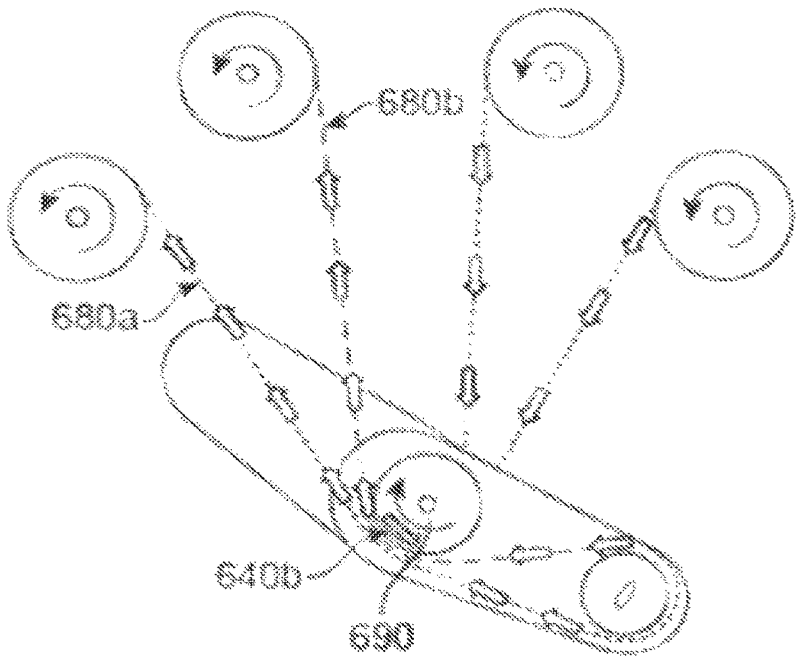
FIG. 6C illustrates an example representation of a different tensile state of the surgical instrument in a master/slave surgical system.

FIGS. 6B and 6C illustrate this process and the following paragraphs further detail the interaction between the inbound and outbound cable segments, the reciprocal pantograph, and the input controller pairs. For clarity, hereafter, the inbound segment of the first cable within the first differential is the first segment 660*a*, the outbound segment of the first cable within the first differential is the second segment 660*b*, the inbound segment of the second cable within the second differential is the third segment 660*c*, and the outbound segment of the second cable within the second differential is the fourth segment 660*d*.

Additionally, the first input controller of the first controller pair controls the length of the first segment 660*a*; the second input controller of the first controller pair controls the length of the second segment 660*b*; the first input controller of the second controller pair controls the length of the third segment 660*c*; and, the second input controller of the second controller pair controls the length of the fourth segment 660*d*. Any pair of cable segments introduced above could be described as an inbound/outbound segment pair depending on the spooling/unspooling being performed on one the input controllers of the pair at that moment in time. In the illustrated embodiment, an inner and an outer input controller (e.g. 520*a* and 520*b*) are paired, but one knowledgeable in the art will appreciate that the input controllers may be configured in different pairings.

In the illustrated embodiment, there are five possible states in attached mode for a given cable of an input controller pair coupled by a differential. In a first state the input controller pair concurrently decreases length of the first segment and increases length of the second segment. In a second state the input controller pair concurrently increases length of the second segment and decreases length of the first segment. In a third state the input controller pair concurrently unspools of the first and second segments, resulting in a compensatory rotation of the reciprocal pantograph about the reciprocal axis to conserve cable length. In a fourth state the input controller pair concurrently spools the first and second segment, resulting in a compensatory rotation of the reciprocal pantograph about the reciprocal axis to conserve cable length. In a fifth "neutral" state the input controller pair does not manipulate the cable segments. In all possible states, the length of the cable from the first input controller to the second controller of an input controller pair is conserved.

FIG. 6B is a planar view of the support bracket which illustrates the input controllers and the reciprocal pantograph in the first state for the cable associated with the first 660*a* and second 660*b* segments. The first input controller 520*a* unspools the cable, increasing length 670*a* (illustrated as an arrow) in the first segment 660*a* while the second input controller 520*b* spools the same cable decreasing length 670*b* of the second segment 660*b*. This yields rotation of the reciprocal member pulley 614 about the tensile axis 630, no rotation of the reciprocal wrist pulley 612 about the reciprocal axis 554, no rotation of the armature 620 about the reciprocal axis 614, and a reciprocal movement of the cables in the operative through-hole 518. In this embodiment of the first state, the contact area 640*a* of the cable in contact with the reciprocal wrist pulley is unchanged. The second state is similar to the first with the first and the second input controllers being reversed.

FIG. 6C is a planar view of the support bracket which illustrates the input controllers and the reciprocal pantograph in the third tensile state. The first input controller of an input controller pair, e.g. an outer input controller 520*a*, pair spools around its spooling axis 556*a* (attempting to decrease the length 680*a* in the first segment 660*a*) while the second input controller, e.g. an inner input controller 520*b*, of the input controller pair spools around its spooling axis 556*b* (attempting to decrease the length 680*a* of the third segment 660*b*). This yields rotation of the reciprocal member pulley 614 about the tensile axis 630, rotation of the reciprocal wrist pulley about the reciprocal axis 558, and rotation of the differential about the reciprocal axis 558. In this embodiment of the third state, the differential rotates 690 about the reciprocal axis 558 by an amount that compensates for the spooling of the cable segments about the input controller pairs such that the contact area 640*b* of the cable with the reciprocal wrist pulley reduces and the total length of the cables in the pantograph is maintained. The fourth state is similar to the third state with the first and the second input controllers simultaneously unspooling the first and second segment with the unspooling offset by a rotation of the differential about the reciprocal axis.

IX. Surgical Effectors

Figure 7A:
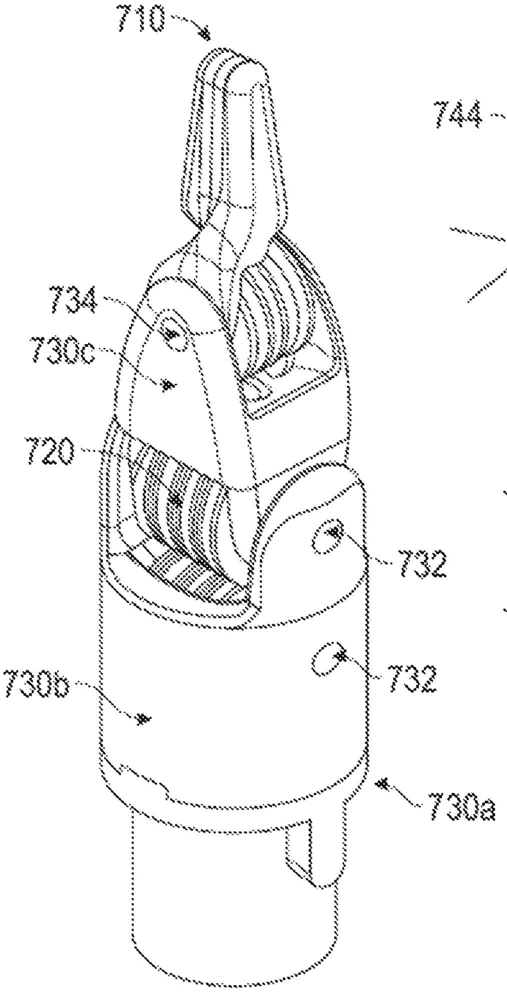
FIG. 7A illustrates an example representation of the surgical effector.
Figure 7B:
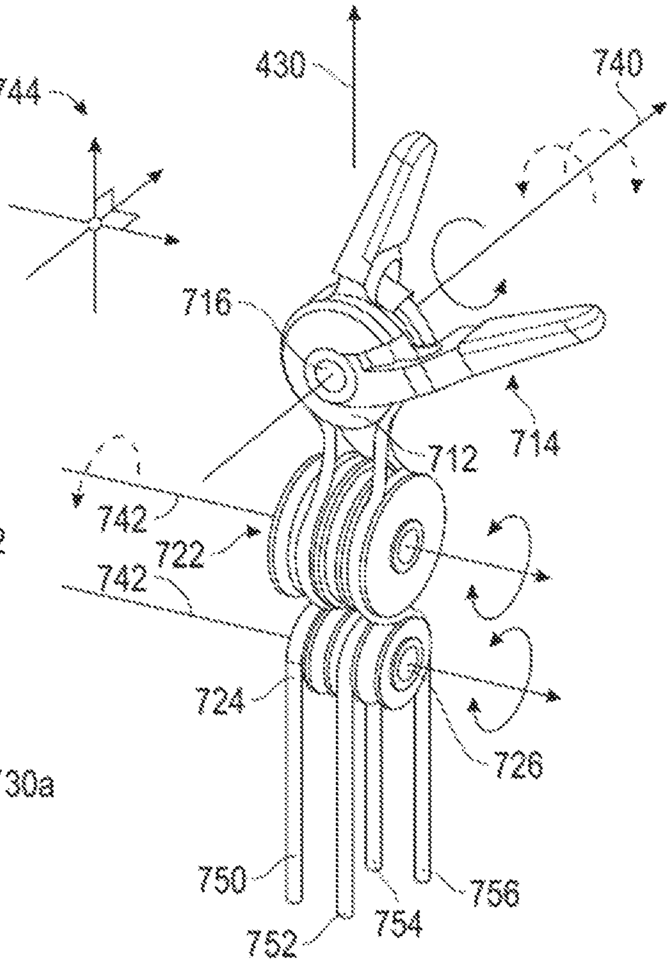
FIG. 7B illustrates an example representation of the surgical effector with the effector housing removed.

FIG. 7A illustrates and embodiment of the surgical effector for laparoscopy in a master/slave surgical system. The surgical effector consists of two working members 710, a surgical wrist 720, and an effector housing 730. FIG. 7B is an illustration of the surgical effector with the effector housing removed.

IX-A. Surgical Effectors Construction

The two working members 710 may be designed as robotic version of an existing surgical tool for performing surgical operations, for example the small robotic forceps illustrated FIGS. 7A and 7B. Each working member consists of a member pulley 712 with a single groove and forceps half 714. The member pulleys have an outer face and an inner face and are able to rotate around a centrally located rotation axis, hereafter the member axis 740, which is orthogonal to the inner and outer faces. The member pulleys may have centrally located member bore 716 coaxial to the member axis passing from the inner face to the outer face and orthogonal to the operation axis 430.

Each forceps half 714 has a substantially flat side and a rounded side, the flat side for interacting with tissues in a surgical operation. The substantially flat side may be textured to allow for easier interaction with tissues in a surgical operation. In another embodiment, the forceps are configured to interact with needles in a surgical procedure. Each forceps half 714 is independently coupled to a member pulley 712 such that the forceps half is normal to the edge of the member pulley and extends radially away from the member axis 740 in the plane of the member pulley 712. The member pulley 712 is further coupled to the forceps half 714 such that the forceps half also rotates around the member axis 740.

The working members 710 are coupled such that the inner faces of the member pulleys are substantially flush with the member bores 716 and member axes 740 being coaxial. The working members 710 are further coupled such that the flat side of each forceps half are facing one another and may be coplanar.

The surgical wrist is a set of two wrist pulleys with four grooves. The first wrist pulley 722 may have a larger radius than the second wrist pulley 724. The wrist pulleys have a front face and a back face and are able to rotate around a centrally located rotation axis that is orthogonal to the front and back faces, hereafter the wrist axes 742. Herein, the four grooves of the wrist pulley will be sequentially referenced as one through four from the back side to the front side. The wrist pulleys 720 may have a centrally located wrist bore 726 coaxial to the wrist axes 742 passing from the front face to the back face of the wrist pulleys. The wrist axes 742 of each wrist pulley are parallel to one another, orthogonal to the member axes 740, and orthogonal to the operation axis 420 such that the three types of axes are an orthogonal set 744. The wrist pulleys are positioned such that the front faces are coplanar, with the first wrist pulley 722 being nearer the action end of the cable shaft 420 along the operation axis 430 than the second wrist pulley 724.

The effector housing 730 may be a cylindrical protective metal sheath which couples the wrist pulleys 720 to the member pulleys 712 while allowing movement of cables 560 through the sheath. In some embodiments, the effector housing may include a proximal clevis 730*b* and a distal clevis 730*c*, the proximal clevis coupled to the distal clevis by a connective pin. The first 720 and second 722 wrist pulleys are coupled to the effector housing 730 by independent set screws 732 that pass from one side of the housing to the other side of the housing along the wrist axes 742 through the wrist bores 726 in the wrist pulleys 720. The member pulleys 712 are coupled to the effector housing by a singular set screw 734 that passes from one side of the housing to the other side of the housing along the coaxial member axes 740 through the central member bores 716 in the member pulleys 712. The member pulleys 712 are further coupled to the effector housing with the forceps halves 714 extending away from the effector housing towards the active end of the cable shaft 420 along the operation axis 430. The housing couples the wrist pulleys 720 and the member pulleys 712 such that the member pulleys are nearer the active end of the cable shaft 720 along the operation axis 430 than the wrist pulleys. The effector housing 730 couples the wrist pulleys 720 and member pulleys 714 to maintain the orthogonal set of the operation axis 430, the member axes 740, and the parallel wrist axes 742, i.e. the outer face of the member pulley 712, the front faces of the wrist pulleys 720, and the operation axis 430 are orthogonal 744.

IX-B. Surgical Effectors Cabling

Within the housing the wrist pulleys 720 and the member pulleys 714 are further coupled by two cables. In some embodiments, the cables within the effector housing are distinct from the two cables coupling the input controllers to the reciprocal pantograph, hereafter referred to as the third and the fourth cable for clarity. For sake of discussion the cables may be described as having inbound and outbound segments, with the inbound segments extending from driver end to the action end within the cable shaft and the outbound segments extending from the action end to the driver end within the cable shaft.

Hereafter, the inbound segment of the third cable is the fifth segment 750*a* and the outbound segment of the third cable is the sixth segment 750*b*. According to one possible cabling scheme, the inbound segment 650*a*, the cable at least partially loops around the second wrist pulley in its first groove. The fifth segment 650*a* then at least partially loops around the first grooves of within the housing the first wrist pulley 722, coupling the first wrist pulley to the second wrist pulley. The inbound segment then at least partially loops around the first groove of the first member pulley 712, coupling the first wrist pulley to the member pulley. The inbound segment 750*a* at least partially looping around the first member pulleys 712 reverses the direction of the cable away from the action end and begins the outbound segment 650*b*. On the outbound segment 650*b*, the cable at least partially loops around the third groove of the first wrist pulley 722. The outbound segment 650*b* then at least partially loops around the third groove of the second wrist pulley 724.

Similarly, the inbound segment of the fourth cable is the seventh segment 750*c* and the outbound segment of the fourth cable is the eighth segment 750*d*. Continuing the same cabling scheme above, the inbound segment 750*c* at least partially loops around the second grooves of the wrist pulleys 720 on the inbound route, at least partially loops around the second member pulley 712 reversing the direction to begin the outbound segment 750*d*, and at least partially loops around the fourth grooves of the wrist pulleys In the illustrated embodiment, the inbound cables at least partially loop one half of the second wrist pulley and the opposite half of the first wrist pulley. It will be obvious to one skilled in the art that these halves may be reversed.

In the illustrated embodiment, the third cable at least partially loops around the wrist pulleys in the first groove on the inbound route and the third groove on the outbound route while the fourth cable at least partially loops around the wrist pulleys in the second groove on the inbound route and the fourth groove on the outbound route. It will be obvious to one skilled in the art that the grooves of the inbound and outbound routes for the third and fourth cables may be configured in a different manner.

Figure 8:
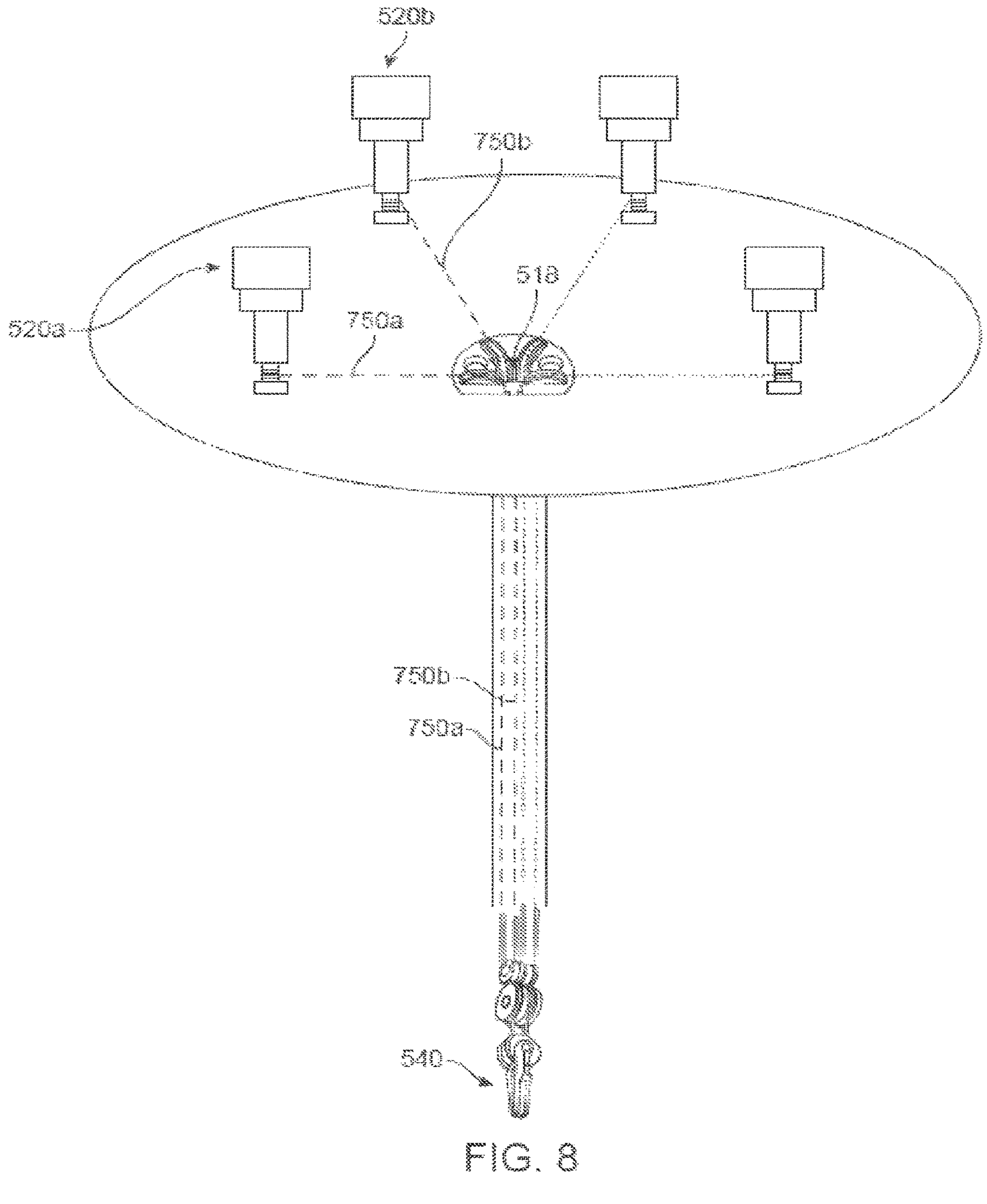
FIG. 8 illustrates an example coupling of the input controllers to the surgical effectors of the surgical instrument in a master/slave surgical system.

FIG. 8 illustrates how the input controllers 520 are coupled to the surgical effector 440. The bottom tier of each input controller 520 is coupled to a rotary joint 570 on the support bracket 410. Each inner input controller and outer input controller pair (e.g. 520*a* and 520*b*) is coupled to the surgical effector 440 by a cable that passes through the operative through-hole 518 such that the inbound segment fifth segment 750*a* of the outer input controller is coupled to the outbound sixth segment 750*b* of the inner input controller via the surgical effector 440. In alternative configurations, the inbound and outbound segments as well as the paired input controllers are interchangeable.

IX-C. Surgical Effector Degrees of Freedom

In the described configuration, the surgical effector has three controllable degrees of freedom: a first yaw angle 910, a second yaw angle 920, and a pitch angle 930 illustrated in FIGS. 9A-9D.

Figure 9A:
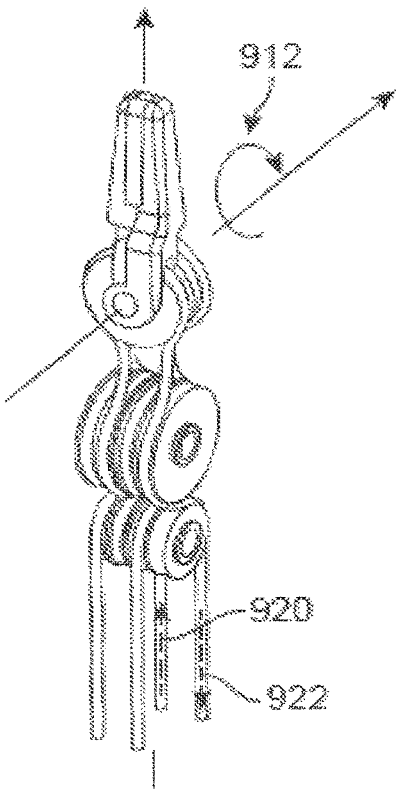
FIG. 9A illustrates an example of the surgical effector in a neutral state.
Figure 9B:
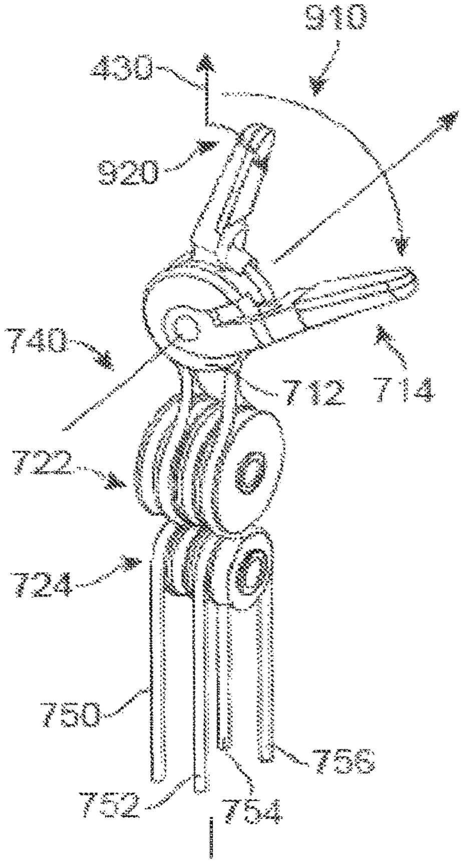
FIG. 9B illustrates the first and second yaw angles of the surgical effector being increased.

As illustrated in FIGS. 9A and 9B, the first degree of freedom is motion of the first forceps half 714 as the first member pulley 712 rotates 912 about the member axis 740, i.e. the yaw axis, moving the forceps half 714 in the plane of the first member pulley such that the forceps half creates a first yaw angle 910 with the operation axis 430.

Similarly, the second degree of freedom is motion of the second forceps half 714 as the second member pulley 712 rotates about the member axis 710, i.e. the yaw axis, moving the second forceps half in the plane of the second member pulley such that the forceps half creates a second yaw angle 920 with the operation axis 430.

Figure 9C:
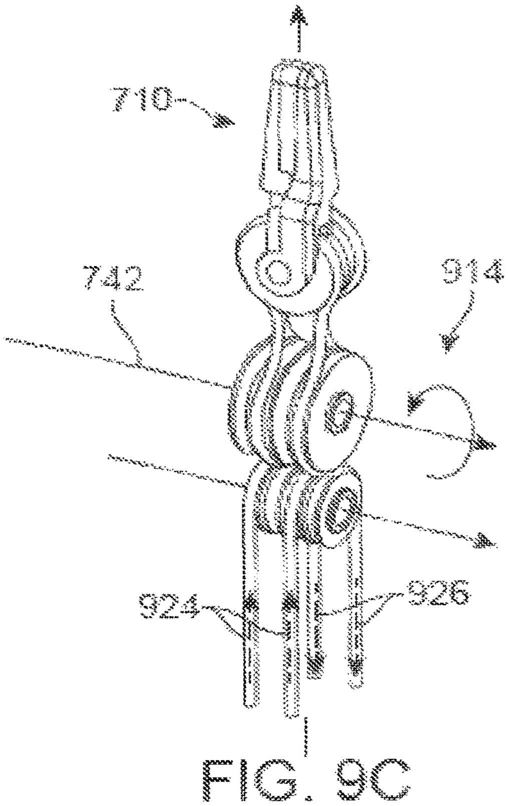
FIG. 9C illustrates a different example of the surgical effector in a neutral state.
Figure 9D:
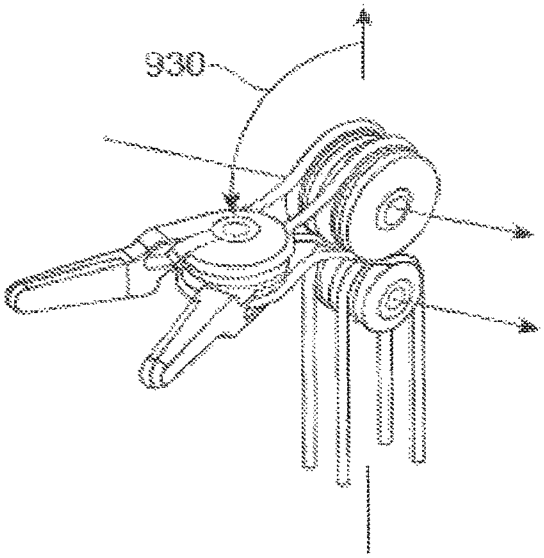
FIG. 9D illustrates the pitch angle of the surgical effector being increased.

As illustrated in FIGS. 9C and 9D, the third degree of freedom is motion of the working members as the first wrist pulley rotates 922 about the first wrist axis 742, i.e. the pitch axis, moving the working members in the plane of the first wrist pulley 722 such that the working members create first yaw angle 920 with the operation axis 430.

In the described embodiment, the first and the second yaw angles are coplanar and the plane of the pitch angle is orthogonal to the plane of the yaw angles. In other embodiments, the first yaw angle, the second yaw angle, and the pitch angle may have different orientations to the operation axis. In still other embodiments, the first and second yaw angles may not be coplanar.

The surgical effector may also move in two additional degrees of freedom: a rotation angle and a translation distance. The rotation angle is created by rotation of the IDM and MCI about the operation axis. The translation distance is created by motion of the robotic arms such that the cable shaft translates along the operation axis.

IX-D. Surgical Effector Movement

Movement about the three degrees of freedom in this system is created by rotation of the member pulleys 714 and the wrist pulleys 720 about their respective axes. The rotation of the pulleys about their axes is caused by the input controllers spooling or unspooling the cables to control the length of the cables.

FIGS. 9A-9D further demonstrate a method for causing motion of the surgical effector about the three controllable degrees of freedom by controlling length in the cables. In this embodiment, each input controller is coupled to either the input or output segment of the third cable or the input or output segment of the fourth cable in the surgical effector. The first input controller of the first controller pair controls the length of the fifth segment 750*a*; the second input controller of the first controller pair controls the length of the sixth segment 750*b*; the first input controller of the second controller pair controls the length of the seventh segment 750*c*; and, the second input controller of the second controller pair controls the length of the eighth segment 750*d*.

FIG. 9A illustrates the surgical effector in an example "neutral" state, i.e. the first yaw angle 910, the second yaw angle 920, and the pitch angle 930 have no offset from the operation axis 430 with no cable segment length being modified. The first yaw angle 910 is manipulated by controlling length in the fourth cable such that the length of the seventh segment increases 920 while the length of the eighth segment decreases 922. This configuration causes the fourth cable to move which in turn causes first member pulley to rotate about the yaw axis 740 such that the first yaw angle 910 between the half forceps 714 and the operation axis 430 increases. In a reciprocal configuration, the first yaw angle 910 can be decreased by decreasing the length of the seventh segment and increasing the length of the eighth segment. In both configurations, the total length of the surgical cable is maintained.

Similarly, the second yaw angle is manipulated by controlling length in the third cable such that the length of the fifth segment 750*a* increases while the length of the sixth segment 750*b* decreases. This configuration causes the fourth cable to move which in turn causes second member pulley to rotate about the yaw axis 740 such that the second yaw angle 920 between the half forceps and the operation axis 430 increases. In a reciprocal configuration, the third cable moves such that the yaw angle can be decreased by increasing the length of the eighth segment and decreasing the length of the seventh segment. Additionally, motion of the forceps halves about the yaw axes can be in either direction away from the operation axis in the plane of member pulleys. In both configurations, the total length of the surgical cable is maintained.

In some embodiments, the manipulation of segment length of the cables creates an additional 'degree of freedom,' such as grip strength. In these embodiments, the motion about the first and second degrees of freedom may limit one another, i.e. one forceps half is unable to change its yaw angle 910 due to the position and yaw angle 920 of the other forceps half. This may occur, for example, due to an object being held between the forceps halves. The amount of electrical load measured in the system when the first and second degrees of freedom limit one another provides a measure of grip strength.

FIG. 9C illustrates the surgical effector in a neutral state, i.e. the first yaw angle 910, the second yaw angle 920, and the pitch angle 930 have no offset from the operation axis 430 with no cable segment being manipulated by an input controller. The pitch angle 930 is manipulated by controlling length in the third and fourth cables. Length in the fifth and sixth segments is increased 924 while length in the seventh and eighth segments is decreased 926 causing the first wrist pulley to rotate 914 about the pitch axis. This configuration causes the third and fourth cables to move which increases the pitch angle between the working members 710 and the operation axis 430 in the plane of the first wrist pulley 722. Rotation of the effectors about the pitch angle compensates for the increasing and decreasing of length of the segments such that the first and second cables are length conservative.

In a reciprocal configuration, the pitch angle can be decreased by decreasing length in the fifth and sixth segments while increasing length in the seventh and eighth segments. In all configurations, the length of the surgical cables is conserved. Additionally, motion of the working members about the pitch axis can be in either direction away from the operation axis in the plane of the wrist pulley.

The above description is a configuration controlling the degrees of freedom in which each movement is asynchronous and controlled independently, e.g. first opening one forceps half and then pitching the wrist, etc. However, in most robotic surgical operations the degrees of freedom are changed simultaneously, e.g. opening the forceps while concurrently rotating their orientation at the surgical site. One skilled in the art will note that simultaneous motion about the three controllable degrees of freedom is accomplished by a more complex control scheme for spooling and unspooling the input controllers to control the four cables and the segment lengths.

In one embodiment, this control scheme is a computer program running on the control base of the master device configured to interpret the motions of the user into corresponding actions of the surgical effector at the surgical site. The computer program may be configured to measure the electric load required to rotate the input controllers to compute the length and/or movement in the cable segments. The computer program may be further configured to compensate for changes in cable elasticity, (e.g. if the cables are a polymer), by increasing/decreasing the amount of rotation needed for the input controllers to change the length of a cable segment. The tension may be adjusted by increasing or decreasing the rotation of all the input controllers in coordination. The tension can be increased by simultaneously increasing rotation, and the tension can be decreased by simultaneously decreasing rotation. The computer program may be further configured to maintain a minimum level of tension in the cables. If the tension in any of the cables is sensed to drop below a lower minimum tension threshold, then the computer program may increase rotation of all input controllers in coordination until the cable tension in all cables is above the lower minimum tension threshold. If the tension in all of the cables is sensed to rise above a upper minimum tension threshold, then the computer program may decrease rotation of all input controllers in coordination until the cable tension in any of the cables is below the upper minimum tension threshold. The computer program may be further configured to recognize the grip strength of the operator based on the load of the motors actuating the input controllers coupled to the cable segments, particularly in a situation where the working members are holding on to an object or are pressed together. More generally, the computer program may be further configured to further control the translation and rotation of the surgical instrument via the robotic arm and IDM.

X. Reciprocal Motion

Figure 10A:
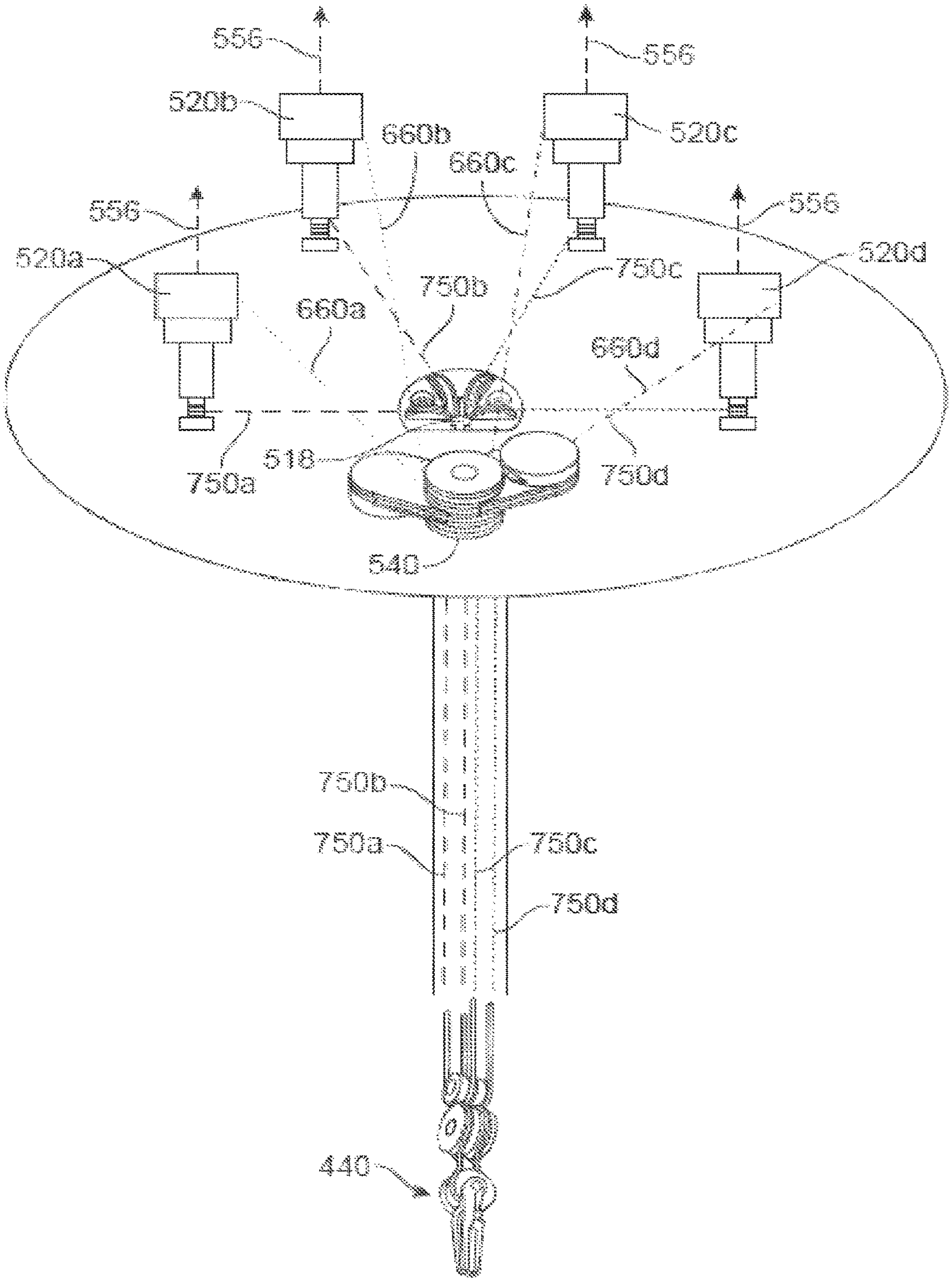
FIG. 10A illustrates an example of the surgical instrument with all cable connections.
Figure 10B:
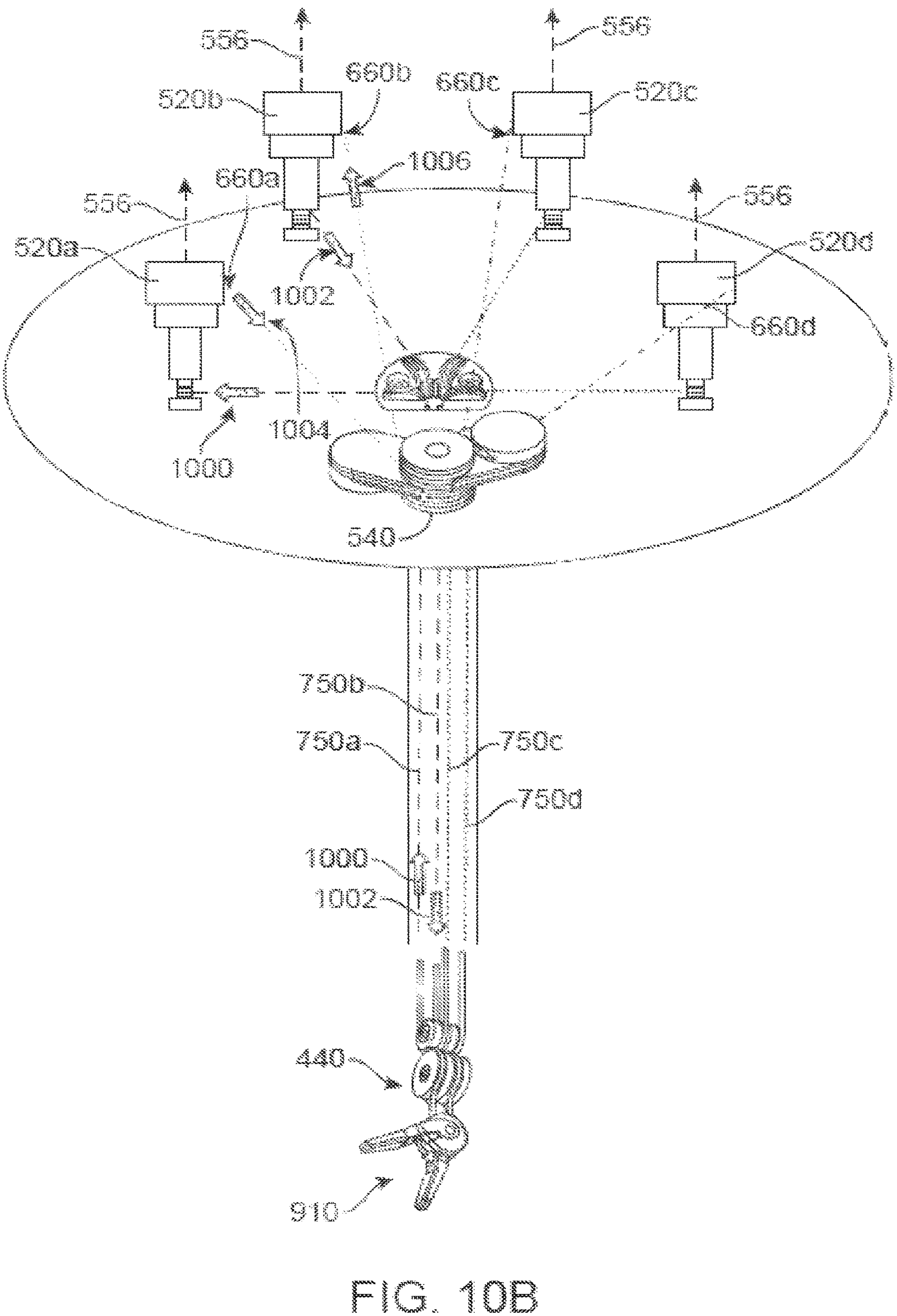
FIG. 10B illustrates an example of reciprocal motion in the surgical instrument when the first yaw angle is increased.
Figure 10C:
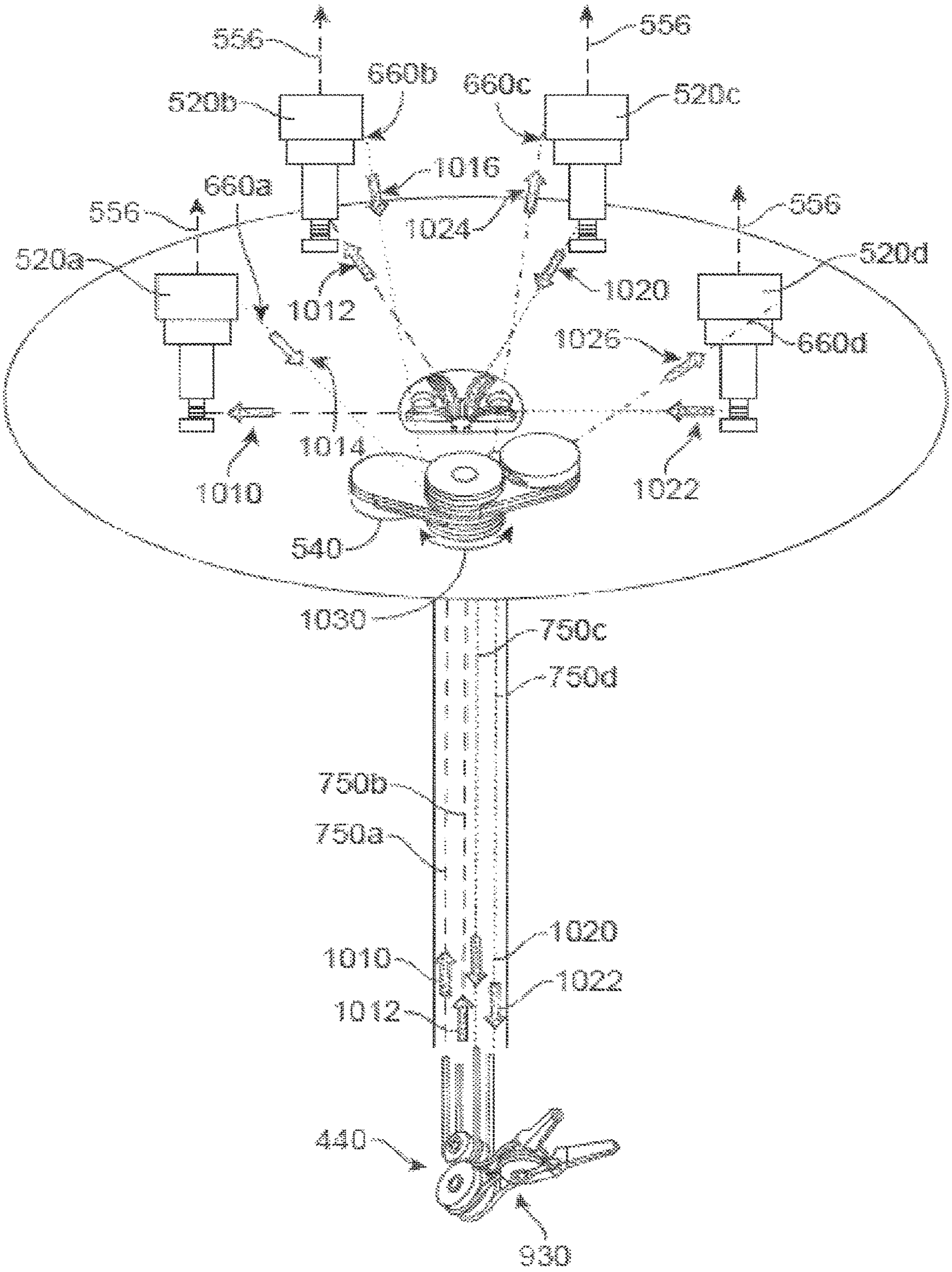
FIG. 10C illustrates an example of reciprocal motion in the surgical instrument when the first pitch angle is increased.

The reciprocal pantograph is configured to mimic the motion of the surgical effector in a reciprocal manner. FIGS. 10A-10C illustrate examples of the reciprocal motion in the surgical instrument.

FIG. 10A illustrates an example wiring of the slave device laparoscope in the neutral state. The outer input controller 520*a* and the inner input controller 520*b* of a first input controller pair are coupled by the first and the third cables and control the spooling and unspooling of cable segments. The first cable couples the input controller pair within the reciprocal pantograph 540 via the first 660*a* and second 660*b* cable segments. The third cable couples the input controller pair within the surgical effector 440 via the fifth 750*a* and sixth 750*b* segment. The length in the first and second cable segments is controlled by rotating the outer 520*a* and inner 520*b* input controllers about their spooling axes 524, respectively. This rotation concurrently changes the length in the fifth and sixth cable segments in a reciprocal manner, respectively, e.g. increasing length in the first segment 750 decreases length in the fifth segment 662, conserving the total cable length between the input controllers.

The inner input controller and the outer input controller of a second input controller pair are coupled by the second and the fourth cables and control the spooling and unspooling of cable segments. The inner input controller 520*c* and the outer input controller 520*d* of a first input controller pair are coupled by the second and the fourth cables and control the segment length. The second cable couples the input controller pair within the reciprocal pantograph 540 via the third 660*c* and fourth 660*d* cable segments. The fourth cable couples the input controller pair within the surgical effector 440 via the seventh 750*c* and eighth 750*d* segment. The length of the third and fourth cable segments is controlled by rotating the inner 520*c* and outer 520*d* input controllers about their spooling axes 524, respectively. This rotation concurrently changes the length of the seventh and eighth cable segments in a reciprocal manner, respectively, e.g. increasing length in the third segment decreases length in the seventh segment.

FIG. 10B shows first an embodiment in which the first yaw angle 910 of the surgical effector 440 is increased. The yaw angle is controlled by spooling and unspooling the first input controller pair, 520*a* and 520*b*, such the length of the fifth segment decreases 1000 while the length of the sixth segment increases 1002. As the yaw angle increases, the length in the first segment increases 1004 while length in the second segment decreases 1006 such that, within the restraint pantograph, the member pulley rotates about the tensile axis. In this configuration, the overall length of the third cable is maintained in the reciprocal pantograph 540, and the length of the first cable is maintained in the surgical effector and cable shaft. The second yaw angle may be manipulated by similarly spooling the second pair of input controllers to manipulate the length of the segments of the third and fourth cables. Either yaw angle may be decreased by manipulating segment lengths with the input controllers in an inverse manner.

FIG. 10C shows an embodiment in which the pitch angle 930 of the surgical effector 440 is increased. The pitch angle of the surgical effector is controlled by unspooling the first cable such that the length of the fifth segment 1010 and length of sixth segment 1012 attempts to increase while simultaneously spooling the second cable such that the length of the seventh segment 1020 and length of eighth segment 1022 attempts to decrease. The change of the pitch angle in the surgical effector compensates for the spooling and unspooling of the cables such that the first and second cables are length conservative. As the pitch angle 930 increases, the length of the first segment 1014 and length of the second segment 1016 increases while length of the third segment 1024 and fourth segment 1026 decreases such that, within the restraint pantograph, the wrist pulleys and armature rotate about the reciprocal axis 1030. In this configuration the overall length of the third cable is maintained in the reciprocal pantograph as discussed previously. The pitch angle may be decreased by manipulating segment length of the cables with the input controllers in an inverse manner.

XI. Detached Mode

While performing surgical operations at the surgical site the reciprocal pantograph and input controllers are operating in attached mode and the input controllers manipulate the degrees of freedom of the surgical effector.

The input controllers and reciprocal pantograph may also operate in detached mode in which the input controllers are configured to maintain the lengths of the cables in the restraint pantograph. This is useful when attaching or detaching the surgical instrument from the IDM and robotic arm. To remove the surgical instrument from the IDM and robotic arm, the cables may be manipulated to achieve a particular length that will be maintained through the period between uses of the surgical instrument.

In another embodiment, the length of the first through fourth cables are controlled during detached mode to achieve a desired result via actuation of a mechanism other than the input controllers; for example, the mechanism may be a switch, a button, a lever, a pin, or similar. In some embodiments, actuation of the alternate mechanism may release any held object from the effectors; move cable positions towards neutral positions; or, move the effectors to a neutral position for removal, etc.

XII. Alternate Embodiments

In an alternative embodiment of attached mode operation, similarly configured to FIG. 6, the restraint pantograph may be physically rotated about the reciprocal axis such that one degree of freedom of the surgical effector may be manipulated. The degree of freedom manipulated depends on how the input controller pairs are coupled.

Figure 11:
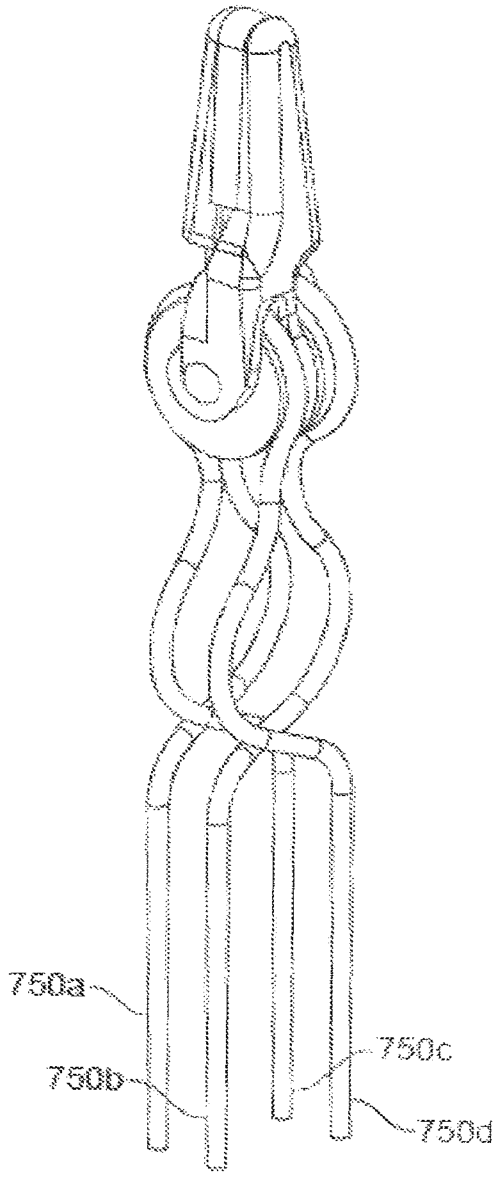
FIG. 11 illustrates an example alternative cabling for the wrist.

FIG. 11 shows the surgical effector with the fifth through eighth cable segments labelled, 750*a*-750*d*. The input controllers are coupled into two pairs by the differential and the surgical effector. With four cable segments there are three distinct pairing possibilities for the two cables in the surgical effector: (1) the fifth and sixth segments pairing the first input controller pair and the seventh and eighth segments pairing the second input controller pair, (2) the fifth and seventh segment pairs the first input controller pair and the sixth and eighth segment pairs the second input controller pair, and (3) the fifth and eighth segment pair the first input controller pair and the sixth and seventh segments part the second input controller pair.

The surgical instrument is configured such that rotation of the reciprocal pantograph spools and unspools the cable segments pairing one input controller pair while reciprocally unspooling and spooling the other input controller pair. With this configuration, rotation of the reciprocal pantograph yields three different motions of the surgical effector depending on the input controller pairings: the first possible pairing yields manipulation of the pitch angle, the second possible pairing yields simultaneous manipulation of both yaw angles in the same direction, and the third possible pairing yields simultaneous manipulation of both yaw angles in opposing directions.

These pairing combinations may be incorporated in to the tool for a potential mechanical override of the surgical instrument in specific situations, e.g. emergency release, power outage etc. For example the third pairing allows for an emergency command to cause the surgical effectors to automatically release an object being held, allowing more rapid removal of the surgical instrument in case of emergency.

XIII. Additional Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method of manipulating a surgical effector of a surgical instrument, the method comprising:

actuating a first input controller to control a length of a first cable segment to move the surgical effector in at least one degree of freedom of movement;

actuating a second input controller to control a length of a second cable segment to move the surgical effector in the at least one degree of freedom of movement; and moving a differential that couples the first and second input controllers together to conserve a length of cable between the first input controller and the second input controller, wherein the differential is part of a pantograph, and wherein actuating the first and second input controllers causes motion in the surgical effector and creates an inverse motion in the pantograph to conserve the length of cable between the first input controller and the second input controller.

2. The method of claim 1 wherein the at least one degree of freedom comprises at least one of pitch, yaw, and grip of the surgical effector.

3. The method of claim 1, wherein actuating the first and second input controllers comprises rotating the first and second input controllers about their respective rotation axes.

4. The method of claim 1, wherein the inverse motion in the pantograph includes rotating at least one armature about a rotation shaft.

5. The method of claim 1, wherein actuating the first and second input controllers comprising actuating a manipulator.

6. The method of claim 1, wherein actuating the first and second input controllers concurrently increase the length of the first cable segment and increase the length of the second cable segment.

7. The method of claim 1, wherein actuating the first and second input controllers concurrently decrease the length of the first cable segment and decrease the length of the second cable segment.

8. A method of operating a surgical wrist that moves with at least N degrees of freedom, the method comprising:

independently operating at least N+1 input controllers that are coupled to at least N+1 surgical cables to control motion of the surgical wrist; and conserving a length of the at least N+1 surgical cables between pairs of the at least N+1 input controllers that are coupled by a reciprocal structure, wherein independently operating the at least N+1 input controllers causes motion of the surgical wrist and creates an inverse motion in the reciprocal structure to conserve the length of the at least N+1 surgical cables between pairs of the at least N+1 input controllers.

9. The method of claim 8, wherein the at least N degrees of freedom comprise at least one of pitch, yaw, and grip of the surgical wrist.

10. The method of claim 9, wherein independently operating the at least N+1 input controllers comprising actuating a manipulator.

11. The method of claim 9, wherein a pair of the at least N+1 input controllers concurrently increase a length of a first cable segment of the at least N+1 surgical cables and increase a length of a second cable segment of the at least N+1 surgical cables.

12. The method of claim 9, wherein a pair of the at least N+1 input controllers concurrently decrease a length of a first cable segment of the at least N+1 surgical cables and increase a length of a second cable segment of the at least N+1 surgical cables.

13. The method of claim 8, wherein independently operating the at least N+1 input controllers comprises rotating the at least N+1 input controllers about respective rotation axes, the rotation of the at least N+1 input controllers causing spooling or unspooling of the at least N+1 surgical cables about the at least N+1 input controllers.

14. The method of claim 13, wherein spooling or unspooling the at least N+1 surgical cables about the at least N+1 input controllers creates motion of the surgical wrist.

15. The method of claim 13, wherein the reciprocal structure comprises a pantograph such that independently operating the at least N+1 input controllers causes motion of the surgical wrist and creates the inverse motion in the pantograph.

16. The method of claim 15, wherein the inverse motion in the pantograph includes rotating at least one armature about a rotation shaft.

17. The method of claim 16, wherein the rotating at least one armature about a rotation shaft includes rotating at least one differential coupled to the at least one armature.

18. A method of operating a surgical instrument having a surgical wrist that moves with at least N degrees of freedom, the method comprising:

in an attached mode where the surgical instrument is attached to a robotic arm, operating at least N+1 input controllers that are coupled to the surgical wrist via first cabling to control motion of the surgical wrist; and, in a detached mode where the surgical instrument is detached from the robotic arm, maintaining cable lengths in the first cabling via motion of a structure in the surgical instrument that is coupled to the at least N+1 input controllers via second cabling distinct from the first cabling.

19. The method of claim 18, wherein the motion of the surgical wrist causes inverse motion in the structure that maintains cable lengths in the first cabling and in the second cabling.

20. The method of claim 18, wherein:

wherein operating the at least N+1 input controllers in the attached mode comprises rotating each of the at least N+1 input controllers about a respective rotation axis by an instrument manipulator of the robotic arm, and wherein maintaining the cable lengths in the detached mode comprises passively maintaining the cable lengths by rotating the structure about a reciprocal axis.

* * * * *